United States Patent [19]

Kosaka

[11] Patent Number: 5,548,395
[45] Date of Patent: Aug. 20, 1996

[54] PARTICLE ANALYZER

[75] Inventor: Tokihiro Kosaka, Kakogawa, Japan

[73] Assignee: Toa Medical Electronics Co., Ltd., Japan

[21] Appl. No.: 937,340

[22] Filed: Aug. 31, 1992

[30] Foreign Application Priority Data

Sep. 20, 1991 [JP] Japan ................................. 3-270106
Sep. 20, 1991 [JP] Japan ................................. 3-270107

[51] Int. Cl.$^6$ .......................... G01N 15/14; G01N 21/23
[52] U.S. Cl. ............................................. 356/73; 356/39
[58] Field of Search ................................. 356/39, 73, 23, 356/417; 382/6, 133

[56] References Cited

U.S. PATENT DOCUMENTS 5,159,642 10/1992 Kosaka ................................. 356/39 X
5,247,340 9/1993 Ogino ..................................... 356/73

Primary Examiner—Vincent P. McGraw
Assistant Examiner—K. P. Hantis
Attorney, Agent, or Firm—Jones, Tullar & Cooper, P.C.

[57] ABSTRACT

A particle analyzer comprising a one-dimensional image sensor for producing imaging signals by scanning a particle in a flow of specimen containing particle components such as blood and urine in a flat sheath flow thin in thickness in the light emitting direction and broad in the direction orthogonal to the light emitting direction, and a signal processing device for processing the signals and operating on the basis of the imaging signals from the one-dimensional image sensor. A particle analyzer excellent in analyzing capability for obtaining morphological information of particles in the liquid specimen flowing in a flow cell in real time is presented. Besides, by emitting light to a flowing particle, the transmitted light image is focused on the one-dimensional image sensor (line sensor), and the detected image signal from the line sensor is further processed in detail in the signal processing device. The signal processing device comprises a background correction processing circuit, a binarizing processing circuit, a binary signal processing circuit, a particle region division processing circuit and an arithmetic circuit. A particle analyzer high in analyzing capability for obtaining the absorption quantity and morphological information of individual particles in the liquid specimen flowing in a flow cell in real time is presented.

17 Claims, 19 Drawing Sheets

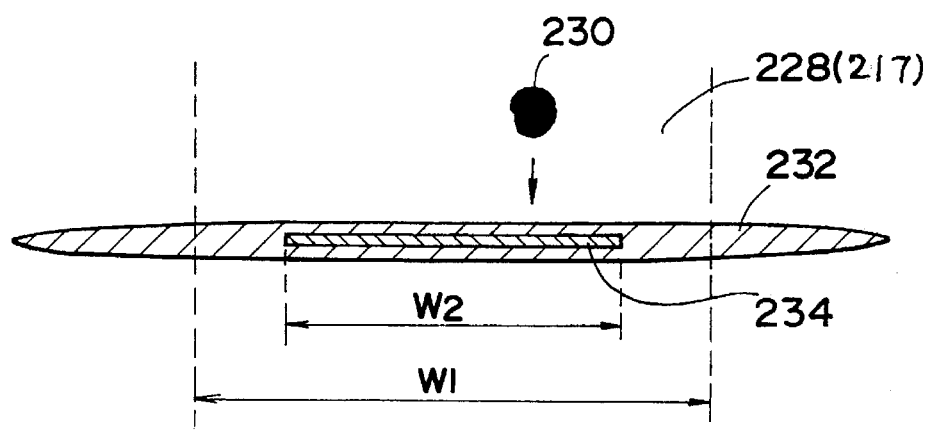
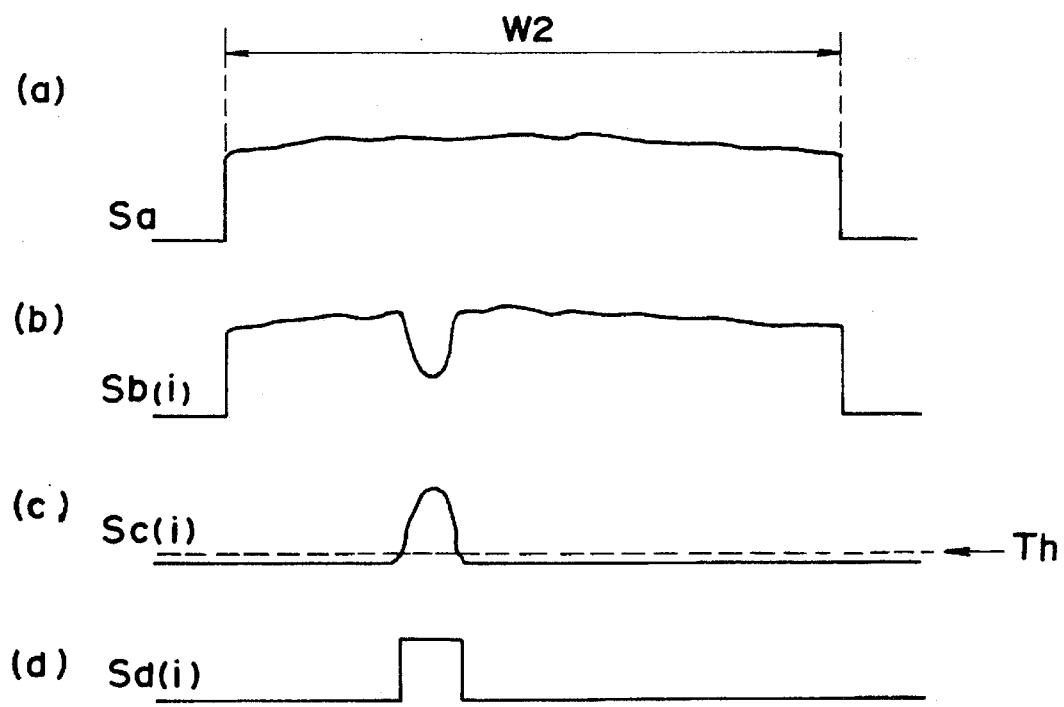
FIG.15

SCANNING CYCLE NUMBER i

PARTICLE ANALYZER

CROSS REFERENCE TO RELATED APPLICATION

This application discloses subject matter which relates to that disclosed in copending application, Ser. No. 08/102,239, filed Aug. 5, 1993.

BACKGROUND OF THE INVENTION

The present invention relates to a flow cytometer, imaging flow cytometer or similar particle analyzer for analyzing a liquid specimen containing particles such as blood and urine, or more particularly to a particle analyzer excellent in analyzing capability and which possesses a detection unit (image sensor) capable of obtaining the morphological information of particles flowing in the flow cell in real time and a signal processing unit, and moreover to an apparatus for analyzing particles by emitting light to the particles in a liquid specimen (blood, urine, or the like) moving as a sheath flow, focusing the transmission light image on a one-dimensional image sensor (line sensor), and processing the obtained detection signal, and more specifically to a particle analyzer capable of obtaining absorption (extinction) information, morphological information and the like of individual particles in real time.

Hitherto, as the particle analyzer using a flow cell, an apparatus as shown in FIG. 1 is known. In this apparatus, laser beams from a laser source 100 are directed to particles flowing in a sheath flow in a flow cell 106, which are optically scanned in a direction which crosses with a particle flow direction (the surface-reverse direction in the sheet) by a polarizer (including a lens) 102. Optical signals obtained from the parts of the particles to be analyzed are detected by optical detectors 114, 116, so that more specific morphological information may be obtained for individual particles. Numeral 104 denotes a controller, 108, 110 are objective lenses, 112 is a dichroic mirror, 118, 120 are A/D converters, and 122 is a signal processor. The sheath flow, meanwhile, refers to a flow surrounded by a suspension of particles covered with a laminar sheath liquid in order to align particles neatly in one row and precisely in the middle of the flow to allow passage.

In order to scan using laser beams, this apparatus requires an expensive light polarizing element (polarizer 102) and its control device (controller 104) utilizing the acousto-optical effect or electro-optical effect. Besides, the laser beams must usually be reduced to a very thin level of 2 μm or less, and it is necessary to scan the laser beam stable and accurately with respect to the flowing position of the particles.

In other prior art, a so-called slit scan apparatus is known, in which laser beams are reduced to about 1 μm and emitted in the flow direction of the particles, and the detection signal waveform of the scattered light or the fluorescence obtained at this time is analyzed to obtain more specific information about the particles. In this apparatus, specific information which divides each particle two-dimensionally is not obtained. That is, it does not possess resolution in the direction vertical to the particle flow direction, and as compared with the apparatus shown in FIG. 1 or the apparatus of the present invention described below, the quantity of information obtained about the particle to be analyzed is smaller, and the precision is lower.

On the other hand, the Japanese Laid-open Patent Hei. 1-270644 discloses a particle analyzer with scanning light beams in a direction crossing the particle passing direction, detecting the light transmitted inside the particle by a photo detector, and obtaining the image information of the particle.

The Japanese Laid-open Patent Hei. 2-105041 discloses a particle measuring apparatus for receiving transmitted light by an array type photo detector disposed at the conjugate position with the detecting part, by improving the apparatus disclosed in the above Japanese Laid-open Patent Hei. 1-270644.

The Japanese Laid-open Patent Sho. 52-113272 discloses an apparatus for scanning a spot light by a flying spot tube in the midst of passing of a biological cell specimen through a flow cell, and obtaining the color information and morphological information (area and shape) of the cell.

The Japanese Laid-open Patent Sho. 62-254037 discloses a construction in which a flow cytometer is furnished with a streak imaging device, where detection of particles by the imaging device are performed almost simultaneously, and an imaging signal is processed only when matched with a predetermined characteristic value, that is, only the particle of specific characteristic is imaged. As the imaging device, sampling imaging by using a one-dimensional image sensor is also unveiled.

The Japanese Laid-open Patent Hei. 3-123840 discloses a construction in which a moving object such as iron ore is taken by a one-dimensional image sensor, and the particle size distribution of the object is determined on the basis of a two-dimensional image data obtained by accumulating a one-dimensional image data.

U.S. Pat. No. 4,338,024 (Application No. 146064) and Japanese Patent Publication Sho. 57-500995 (the original application being the above U.S. patent application Ser. No. 146064) relate to a construction in which a flat sample liquid flow is formed, that is, a flat sheath flow is formed, and particle images are taken.

In the apparatus disclosed in the Japanese Laid-open Patents Hei. 1-270644, Hei. 2-105041 and Sho. 52-113272, light beams are scanned, and special devices are needed, yet stable scanning is difficult.

The apparatus disclosed in Japanese Laid-open Patent Hei. 3-123840 relates to an apparatus for measuring the particle size of material such as iron ore charged in a blast furnace. The field of this apparatus thus differs from that of the present invention. Incidentally, nothing is mentioned about real time processing of the accumulated image data or determination of parameters such as absorption quantity, area and peripheral length.

In the Japanese Laid-open Patents Sho. 62-254037 and Hei. 3-123840, nothing is mentioned about the flat flow of a sample liquid flow. By flat flow, the quantity of analysis may be increased.

U.S. Pat. No. 4,338,024 and Japanese Patent Publication Sho. 57-500995 refer to forming of flat sample liquid flow as stated above, but the provision of a "one-dimensional image sensor for producing an image signal upon every scanning by forming a flat sample liquid flow, and processing means for processing signal and operating on the basis of the image signal from the sensor" is not mentioned in any one of these seven patent publications.

Besides, as the apparatus for extracting and analyzing the features of particles moving in a fluid, the flow cytometer and cell sorter have been hitherto known widely.

In the conventional flow cytometer, the morphological information of particles (area, circumferential length, etc.)

could not be obtained. By passing the specimen in a flat sheath flow, emitting a strobe light, and processing the image taken by a video camera, the absorption quantity and morphological information of particles may be obtained in real time, but it requires a video camera and an exclusive image processing device, which means a higher cost. Yet, since the strobe light is emitted to image at a specific interval of one frame period (1/30 second) of the video camera, particles of low concentration cannot be captured on all image frames at high efficiency. Hence, there are problems in the sample processing ability and repeatability or accuracy of results of the analysis.

U.S. Pat. No. 4,338,024 and Japanese Patent Publication Sho. 57-500995 refer to forming of flat sample liquid flow as stated above, but none of these seven publications mentions anything about "the one-dimensional image sensor for producing an image signal upon every scanning by forming a flat sample liquid flow, and determination of absorption quantity and morphological information of the particle by processing the signal on the basis of the image signal from this sensor, and determination of the information in real time every time the particle passes through the detection unit".

OBJECT AND SUMMARY OF THE INVENTION

It is hence a primary object of the present invention to provide a particle analyzer of higher precision which is capable of obtaining morphological information and absorption information of particles in real time, in addition to the optical features of particles (scattered light intensity, fluorescent intensity, etc.) obtained in conventional apparatus.

It is another object of the present invention to provide a particle analyzer capable of obtaining absorption information and morphological information and the like of particles in real time, by emitting light to flowing particles, focusing the transmitted light image on a one-dimensional image sensor (line sensor), and analyzing and processing the detection signals from the line sensor in further detail.

To achieve the above objects, the present invention presents a first particle analyzer for discharging a liquid specimen containing particles to be analyzed from the nozzle of a flow cell, forming a sheath flow by passing a sheath liquid around the liquid specimen, emitting light to the liquid specimen flow, detecting the light from the particles, and analyzing the particles on the basis of the detected signal, wherein the liquid specimen flow is a flat flow thin in thickness in the light emitting direction, and broad in the direction orthogonal to the light emitting direction, and it further comprises
a one-dimensional image sensor disposed to extend in a direction vertical to the particle flow direction, and producing an image signal at every scanning cycle for the particle, as the transmitted light image of the particle is focused, and
signal processing means for processing signals and operating on the basis of the image signal from the one-dimensional image sensor.

The present invention presents a second apparatus, conforming to the first apparatus, further comprising a second light source (for example, a strobe light source), and second imaging means for capturing the two-dimensional still image of the particle, wherein a one-dimensional imaging region of the one-dimensional image sensor is formed so as to cross the particle flow, in a two-dimensional imaging region of the second imaging means (e.g. video camera) in the liquid specimen flow, and the signal processing means detects the arrival of a particle on the basis of the imaging signal at least from the one-dimensional image sensor, thereby controlling illumination of the second light source for capturing a two-dimensional still image.

The present invention presents a third apparatus, conforming to the first or second apparatus, further comprising means for detecting the passing of plural particles simultaneously in an imaging region of the one-dimensional sensor, so that the data concerning the scattered light and fluorescent light emitted from the particles and detected are ignored when plural particles pass simultaneously.

In the first or second apparatus, the signal processing means preferably obtains the particle morphological information and/or absorption information on the basis of the imaging signal from the one-dimensional image sensor.

Preferably the morphological information is selected from the cell area, cell circumferential length, nucleus area, cell width, complicatedness in cell (complicated amount/area), cell roundness, and nucleus area rate.

Preferably the absorption information is selected from the absorption quantity and absorbance (absorbtive degree) (absorption quantity/area).

In the above particle analyzers, the sample is led into a flow cell, and the sheath liquid is supplied to form a flat sheath flow. A laser beam from a laser source is emitted to a flat sample flow, and when the particle to be detected crosses the imaging area of the line sensor, the exposure to the line sensor is weakened.

Consequently, the image of the light transmitted through the particle to be detected is focused on the surface of the line sensor, and the signals corresponding to the exposure quantity, for each picture element of the line sensor, are generated sequentially.

The detected signal by the line sensor is processed in the signal processing means, and the morphological information and/or absorption information of the particles is obtained in real time.

The present invention presents a fourth particle analyzer comprising a light source for emitting light to the particle in the liquid specimen moving as a sheath flow, a one-dimensional image sensor disposed to extend in a direction vertical to the moving direction of a particle, and producing an imaging signal at every scanning cycle (i) for the particle, as the transmitted light image transmitting through the particle is focused, and
a signal processing device for obtaining feature parameters of individual particles by processing the imaging signal, thereby analyzing the particles on the basis of the difference of the feature parameters of each particle, wherein
the signal processing means comprises:
background correction processing means for obtaining the correction data $Sc(i)$, by calculating the difference between background data $Sa$ obtained from the image signal in the absence of a particle, and measured data $Sb(i)$ obtained from the image signal when the particle is passing through the imaging region,
binarizing means for obtaining binary signal $Sd(i)$ for detecting the specified portion of the particle (entire particle, or particle nucleus, which may be detected by varying the threshold data) by comparing the correction data $Sc(i)$ with specified threshold data, binary signal processing means for logical operation of the binary signal, and arithmetic means for calculating the feature parameters of particles by the data obtained from the above means.

The present invention presents a fifth apparatus, conforming to the fourth embodiment, further comprising first processing means for obtaining an AND signal S3(i) by a logical AND operation between a binary signal S2(i) of scan cycle (i) and a binary signal S2(i−1) of one scan cycle before (i−1), and means for calculating the sum of the widths of the AND signal pulses corresponding to one particle (e.g. counter CNT1), mens for setting particle moving extent data L in one scanning period (e.g. dip switch DIPSW), and arithmetic means for multiplying these two pieces of data (e.g. lookup table LUT1), whereby the area data is obtained.

The present invention presents a sixth apparatus, conforming to the fourth apparatus, further comprising second processing means for obtaining EXOR signal S6(i) by an exclusive-or operation between the binary signal S2(i) of the scan cycle (i) and the binary signal S2(i−1) of one scan cycle before (i−1), means for calculating the width of each EXOR signal pulse (e.g. counter CNT3), means for setting the particle moving extent data L in one scanning period (e.g. dip switch DIPSW), arithmetic means for calculating the square root of the squared sum of both data in every EXOR signal pulse (e.g. lookup table LUT3), and arithmetic means (e.g. accumulator ACC) for obtaining the cumulative sum of the same particle of the square root data from the arithmetic means, whereby circumferential length data is obtained.

The present invention presents a seventh apparatus, conforming to the fourth apparatus, further comprising second processing means for obtaining EXOR signal S6(i) by an exclusive-or operation between the binary signal S2(i) or scan cycle (i) and binary signal S2(i−1) of one scan cycle before (i−1), means for calculating the sum of the widths of EXOR signal pulses corresponding to one particle (e.g. counter, not shown), and arithmetic means for dividing the above data by 2, whereby the width in the direction vertical to the moving direction is obtained.

The present invention presents an eighth apparatus, conforming to the fourth apparatus, further comprising arithmetic means for obtaining the cumulative sum of the corrected data S1(i) corresponding to one particle (e.g. accumulator, not shown), thereby obtaining absorption quantity data.

The present invention presents a ninth apparatus, conforming to the fourth apparatus, further comprising third processing means for obtaining an AND signal S3(i) in scan cycle (i) by a logical AND operation between the binary signal S2(i) of scan cycle (i) and a binary signal S2(i−1) of one scan cycle before (i−1), and obtaining ANEX signal S7(i) by an exclusive-or operation between the AND signal S3(i) of scan cycle (i) and AND signal S3(i−1) of one scan cycle before (i−1), and means for calculating the width for obtaining the ANEX signal pulse (e.g. counter, not shown), means for setting the particle moving extent data in one scanning period (e.g. dip switch DIPSW), arithmetic means for calculating the square root of the squared sum of both data in every ANEX signal pulse (e.g. lookup table, not shown), and arithmetic means for obtaining a cumulative sum for one particle of square root data from the arithmetic means (e.g. accumulator, not shown), whereby circumferential length data is obtained.

The present invention presents a tenth apparatus, conforming to the fourth apparatus, further comprising third processing means for obtaining an AND signal S3(i) in scan cycle (i) by a logical AND operation between the binary signal S2(i) of scan cycle (i) and a binary signal S2(i−1) of one scan cycle before (i−1), and obtaining an ANEX signal S7(i) by an exclusive-or operation between the AND signal S3(i) of scan cycle (i) and the AND signal S3(i−1) of one scan cycle before (i−1), means for obtaining the sum of the width of ANEX signal pulses corresponding to one particle (e.g. counter, not shown), and arithmetic means for dividing the above data by 2, whereby the width data in the direction vertical to the moving direction is obtained.

The present invention presents an eleventh apparatus, conforming to the fourth apparatus, further comprising two signal processing means for obtaining binary signals by two different threshold data Th1, Th2, obtaining a binary signal S2(i) for detecting the entire particle and a binary signal S4(i) for detecting the nucleus portion of the particle, and obtaining AND signals S3(i), S5(i) by a logical AND operation between binary signals S2(i), S4(i) of scan cycle (i), and binary signals S2(i−1), S4(i−1) of one scan cycle before (i−1), corresponding to these two kinds of signals, and means for calculating the sum of the widths of the AND signal pulses corresponding to one particle as the particle area data and nucleus area data (e.g. counters CNT1, CNT2), and arithmetic means for dividing the nucleus area data by the particle area data (e.g. lookup table LUT2), whereby the nucleus area rate data is obtained.

The present invention presents a twelfth apparatus, conforming to the fourth apparatus, further comprising arithmetic means for obtaining the cumulative sum of the corrected data S1(i) corresponding to the portion of the nucleus of the individual particles, thereby obtaining the absorption quantity data of the nucleus portion.

The present invention presents a thirteenth apparatus, conforming to the fifth apparatus, further comprising differentiating means for obtaining the difference of the adjacent data on the time axis of the corrected data S1(i), means for calculating the sum of the differential data of the portion corresponding to one particle, or the sum of the square of the differential data as the complicated quantity data (e.g. accumulator, not shown), and arithmetic means for dividing the complicated quantity data by the area data from the arithmetic means (e.g. lookup table LUT1) (e.g. lookup table, not shown), thereby obtaining the complicated degree (complexity) data per unit area.

The present invention presents a fourteenth apparatus, conforming to the sixth or ninth apparatus, further comprising arithmetic means (e.g. lookup table LUT4) for squaring the circumferential length data from the arithmetic means for calculating the circumferential length (e.g. accumulator) and dividing by the area data from the arithmetic means for calculating the area (e.g. lookup table), thereby obtaining roundness (round shape degree) data.

Furthermore, the present invention presents a fifteenth apparatus, conforming to the fourth to the fourteenth apparatuses, further comprising plural sets of arithmetic means so that feature parameters of particles may be calculated simultaneously if plural particles simultaneously cross the imaging area of the one-dimensional image sensor.

In the fourth to the fifteenth apparatuses of the present invention, the diluted and stained (dyed) specimen is led into a flat sheath flow cell, and a sheath liquid is supplied to form a flat sheath flow. The light from the light source is emitted to the flat sample flow, and when the particle to be analyzed crosses this light, the exposure to the line sensor is weakened.

Consequently, the image of the light transmitted through the particle to be detected is focused on the surface of the line sensor, and the signals corresponding to the exposure quantity, for each picture element of the line sensor, are generated sequentially.

The detected signal by the line sensor is subjected to signal processing, background correction processing, binarizing, binary signal processing, particle region division processing, arithmetic operation, etc., and the data is analyzed, and the absorption information, morphological information and others of each particle are obtained in real time.

BRIEF DESCRIPTION OF THE DRAWINGS

FIG. 14 is an explanatory diagram showing the light emitting area, and the detection area of the one-dimensional image sensor (line sensor) in FIG. 13.

FIG. 15 is an example of a waveform diagram of background correction processing for the detected signal by the line sensor.

DETAILED DESCRIPTION OF THE PREFERRED EMBODIMENTS

Figure 1:
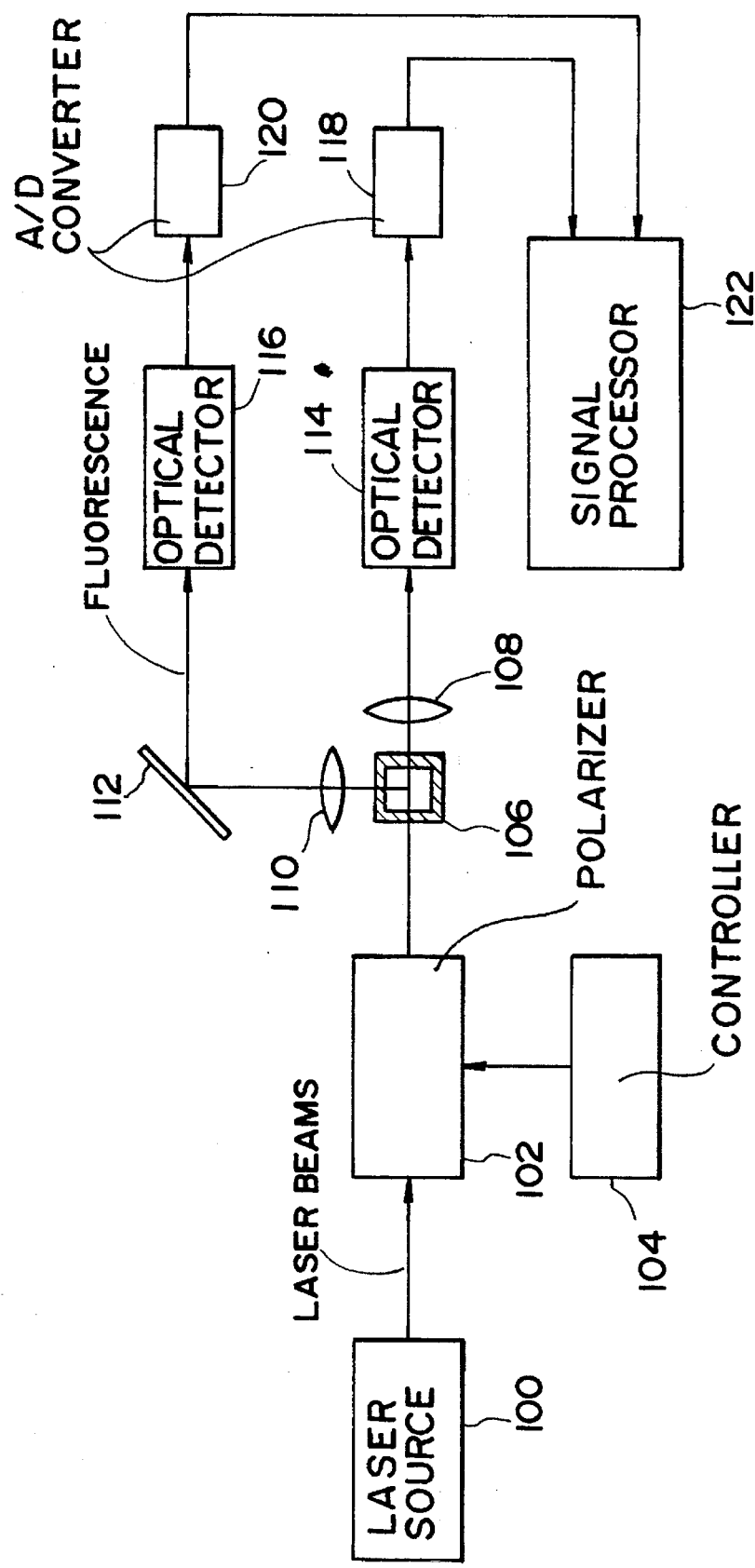
FIG. 1 is an explanatory view partly in block diagram form showing an example of a conventional particle analyzer.

Referring now to the drawings, some of the preferred embodiments of the present invention are described in detail below.

Figure 2:
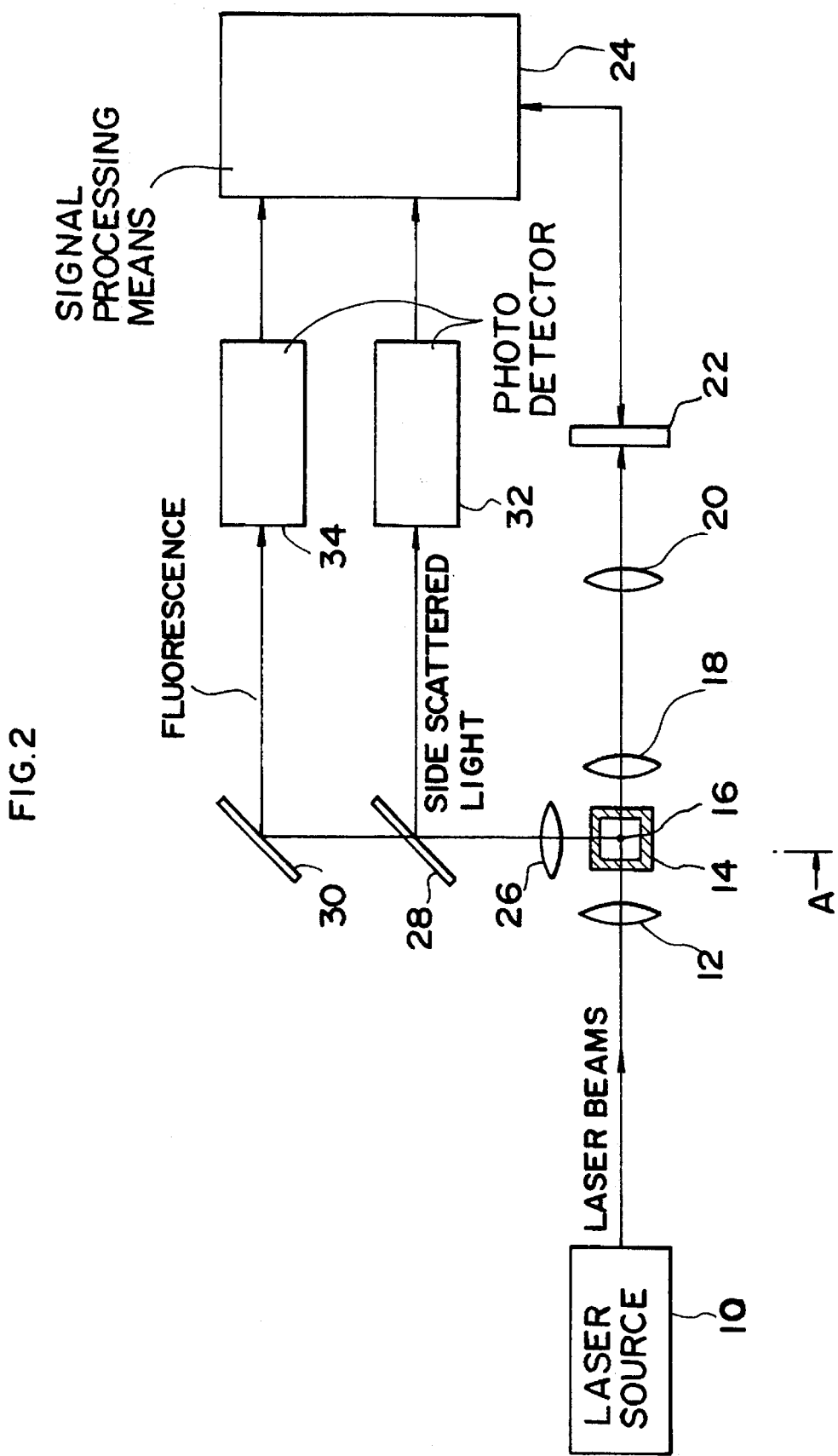
FIG. 2 is an explanatory view partly in block diagram form showing the arrangement of a particle analyzer according to one embodiment of the present invention.

FIG. 2 shows a particle analyzer for discharging a liquid specimen containing particles to be analyzed from the nozzle of a flow cell, forming a sheath flow by passing a sheath liquid around the liquid specimen, emitting light to the liquid specimen flow, detecting the light from the particles in the flow, and analyzing the particles on the basis of the detected signal, wherein the liquid specimen flow is a flat flow thin in thickness in the light emitting direction, and broad in the direction orthogonal to the light emitting direction. The analyzer further comprises:
a one-dimensional image sensor 22 disposed to extend in a direction vertical to the particle flow direction, and producing an image signal at every scanning cycle for the particle, as the transmitted light image of the particle is focussed, and
signal processing means 24 for processing signals and operating on the basis of the image signal from the one-dimensional image sensor 22.

Figure 9:
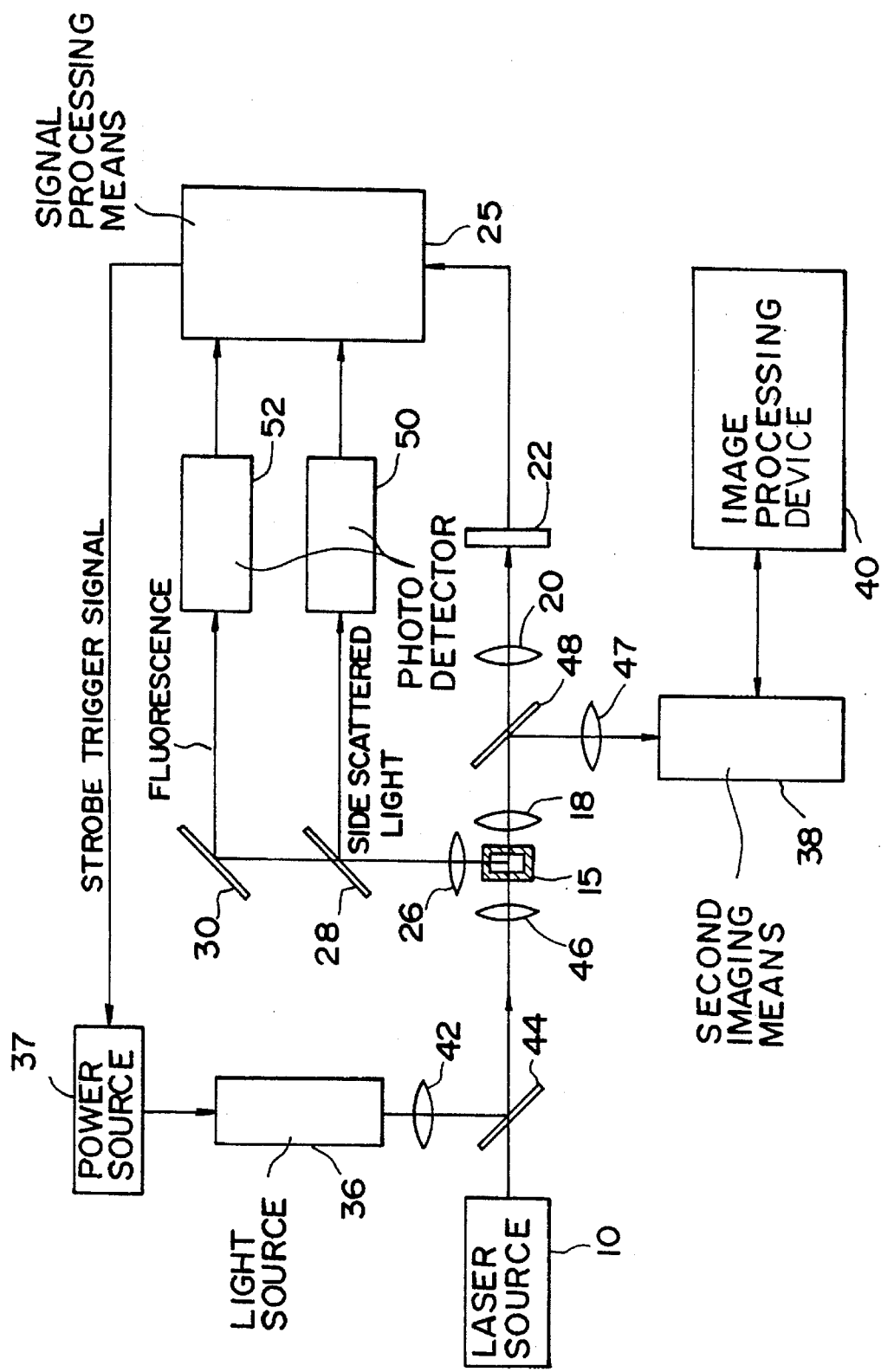
FIG. 9 is an explanatory view partly in block form showing the arrangement of a particle analyzer according to another embodiment of the present invention.

FIG. 9 shows an apparatus conforming to the apparatus noted above. This apparatus further comprises a second light source (for example, a strobe light source) 36, and second imaging means 38 for capturing a two-dimensional still image of the particle, wherein
a one-dimensional imaging region 56 (FIG. 10) of the one-dimensional image sensor 22 is formed so as to cross the flow of particles, in a two-dimensional imaging region 54 of the second imaging means (e.g. video camera) 38 in the liquid specimen flow, and
the signal processing means detects particle arrival on the basis of the imaging signal at least from the one-dimensional image sensor 22, thereby controlling illumination of the second light source 36 for capturing a two-dimensional still image.

The apparatus further comprises means for detecting passing of plural particles simultaneously in an imaging region 56 of the one-dimensional sensor 22, so that the data concerning the scattered light or fluorescent light emitted from the particle and detected are ignored when plural particles pass simultaneously.

In the apparatus shown in FIG. 2 or FIG. 9, the signal processing means preferably obtains the particle morphological information and/or absorption information on the basis of the imaging signal from the one-dimensional image sensor 22.

The sample is led into a flow cell 14 or 15, and sheath liquid is supplied to form a flat sheath flow. The laser beam from a laser source 10 is emitted to the flat sample flow, and when the particle to be detected crosses the imaging area of the line sensor 22, the exposure to the line sensor is weakened.

Consequently, the image of the light transmitted through the particle to be detected is focused on the surface of the line sensor 22, and the signals corresponding to the exposure quantity for each picture element of the line sensor 22 are generated sequentially.

The detected signal by the line sensor 22 is processed in the signal processing means 24 or 25, and the morphological information and/or absorption information of the particles is obtained in real time.

Figure 13:
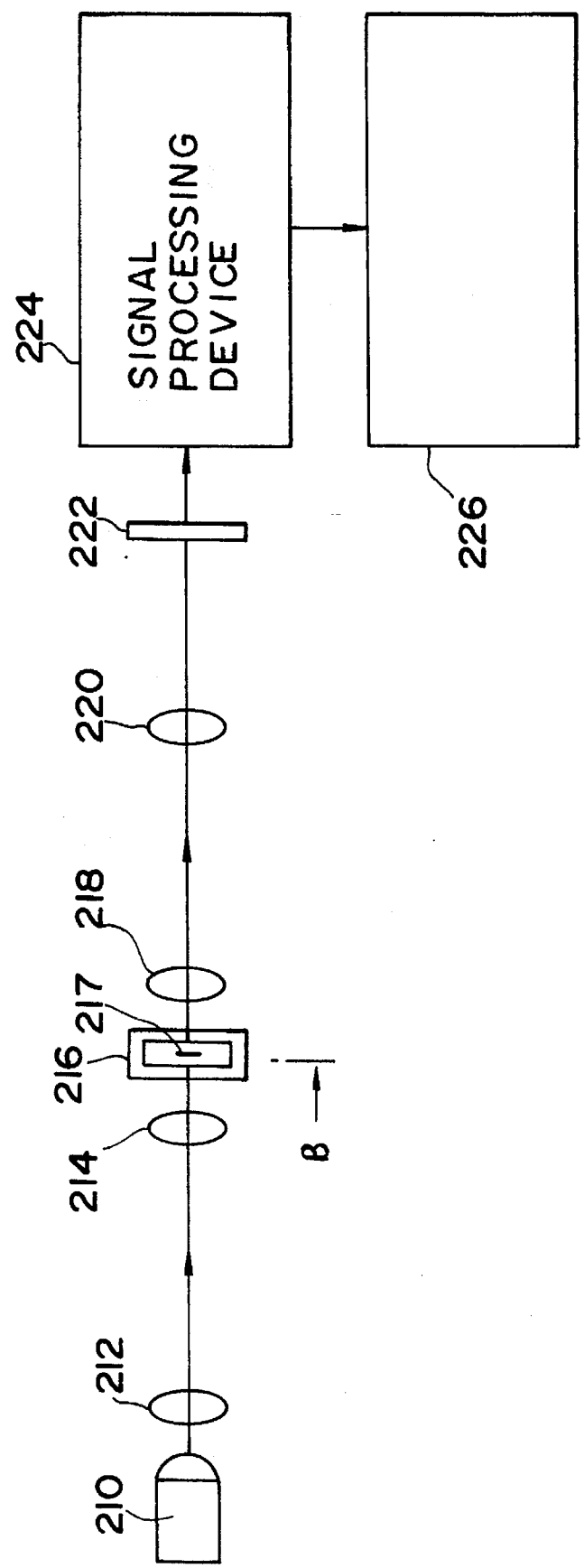
FIG. 13 is an explanatory view partly in block diagram form showing the arrangement of a particle analyzer according to a different embodiment of the present invention.
Figure 26:
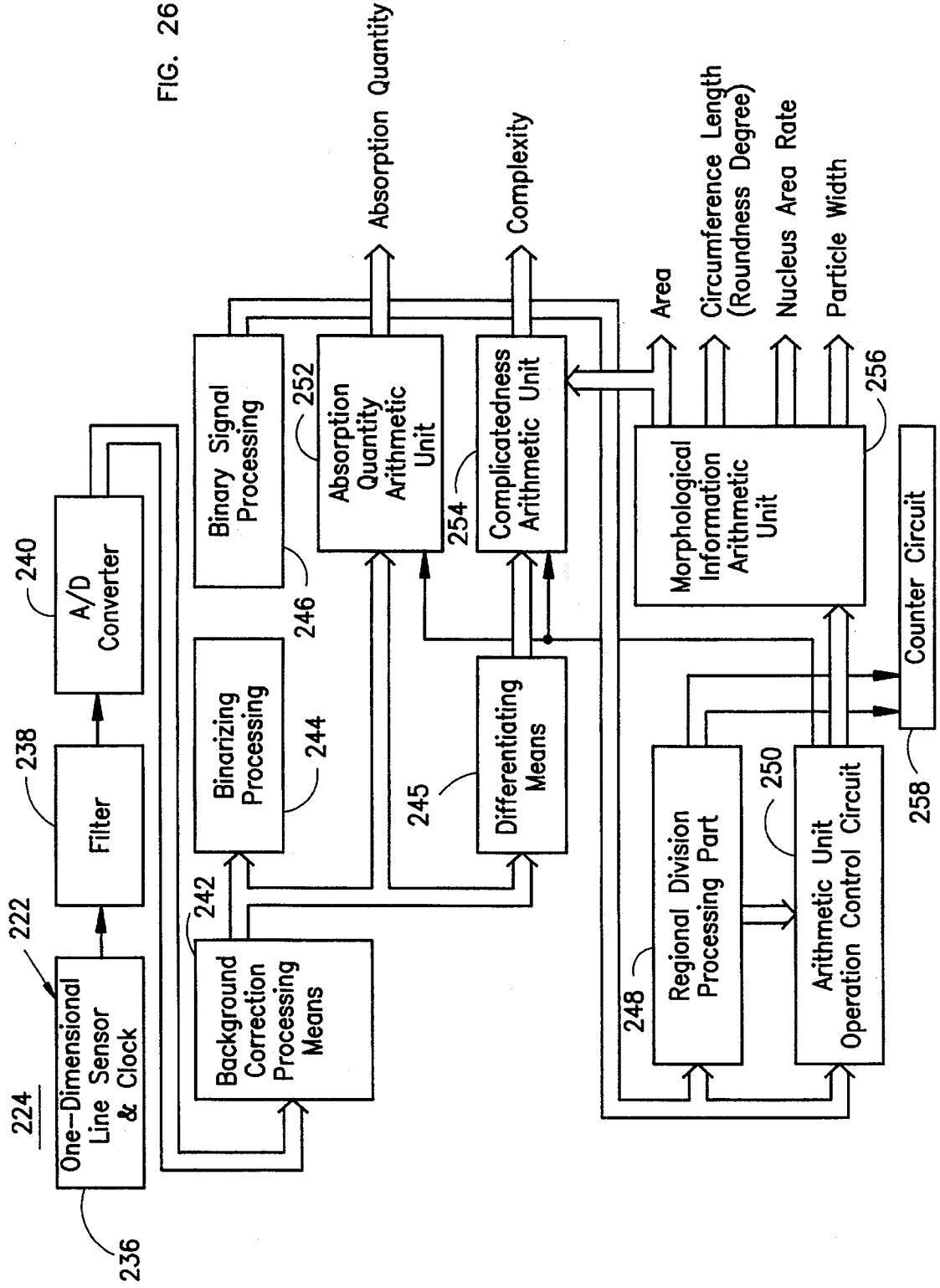
FIG. 26 is a block diagram showing an example of a signal processing device.

As shown in FIG. 13 and FIG. 26, a particle analyzer comprises a light source 210 for emitting light to the particle in the liquid specimen moving as a sheath flow, a one-dimensional image sensor 222 disposed to extend in a direction vertical to the moving direction of the particles, and producing an imaging signal at every scanning cycle (i) for the particle, as the transmitted light image transmitting through the particle is focused, and a signal processing device 224 for calculating feature parameters of individual particles by processing the imaging signal, thereby analyzing the particles on the basis of the difference of the feature parameters of each particle, wherein the signal processing device 224 comprises:

background correction processing means 242 which obtains a correction data Sc(i) by calculating the difference between the background data Sa obtained from the image signal in the absence of a particle and the measured data Sb(i) obtained from the image signal when a particle is passing through the imaging region, binarizing means 244 for obtaining a binary signal Sd(i) for detecting the specified portion of the particle (entire particle, or particle nucleus, which may be detected by changing the threshold data) by comparing the correction data Sc(i) with specified threshold data, binary signal processing means 246 for the logical operation for binary signal, and arithmetic means for calculating the feature parameters of particles from the data obtained by the above means.

The apparatus further comprises first processing means for obtaining an AND signal S3(i) by a logical AND operation between the binary signal S2(i) of scan cycle (i) and a binary signal S2(i−1) of one scan cycle before (i−1), and means for calculating the sum of the widths of the AND signal pulses corresponding to one particle (e.g. counter CNT1), means for setting the particle moving extent data L in one scanning period (e.g. DIP switch DIPSW), and arithmetic means for multiplying these two pieces of data (e.g. lookup table LUT1), whereby the area data is obtained.

The apparatus further comprises second processing means for obtaining an EXOR signal S6(i) by an exclusive-or operation between the binary signal S2(i) of scan cycle (i) and the binary signal S2(i−1) of one scan cycle before (i−1), means for calculating the width of each EXOR signal pulse (e.g. counter CNT3), means for setting the particle moving extent data L in one scanning period (e.g. dip switch DIPSW), arithmetic means for calculating the square root of the squared sum of both data for every EXOR signal pulse (e.g. lookup table LUT3), and arithmetic means for obtaining the cumulative sum of the same particle of the square root data from the arithmetic means (e.g. accumulator ACC), whereby circumferential length data is obtained.

The apparatus further comprises second processing means for obtaining an EXOR signal S6(i) by an exclusive-or operation between the binary signal S2(i) of scan cycle (i) and the binary signal S2(i−1) of one scan cycle before (i−1), means for calculating the sum of widths of the EXOR signal pulses corresponding to one particle (e.g. counter, not shown), and arithmetic means for dividing the above data by 2, whereby the width in a direction vertical to the moving direction is obtained.

The apparatus further comprises arithmetic means for obtaining the cumulative sum of the corrected data S1(i) corresponding to one particle (e.g. accumulator, not shown), thereby obtaining absorption quantity data.

The apparatus further comprises third processing means for obtaining an AND signal S3(i) in scan cycle (i) by a logical AND operation between the binary signal S2(i) of scan cycle (i) and the binary signal S2(i−1) of one scan cycle before (i−1), and obtaining an ANEX signal S7(i) by an exclusive-or operation between the AND signal S3(i) of scan cycle (i) and the AND signal S3(i−1) of one scan cycle before (i−1), and means for calculating the width for obtaining the ANEX signal pulse (e.g. counter, not shown), means for setting the particle moving extent data in one scanning period (e.g. dip switch DIPSW), arithmetic means for calculating the square root of the squared sum of both data in every ANEX signal pulse (e.g. lookup table, not shown), and arithmetic means for obtaining a cumulative sum for one particle of square root data from the arithmetic means (e.g. accumulator, not shown), whereby circumferential length data is obtained.

The apparatus further comprises third processing means for obtaining an AND signal S3(i) in scan cycle (i) by a logical AND operation between the binary signal S2(i) of scan cycle (i) and the binary signal S2(i−1) of one scan cycle before (i−1), and obtaining an ANEX signal S7(i) by an exclusive-or operation between the AND signal S3(i) of scan cycle (i) and the AND signal S3(i−1) of one scan cycle before (i−1), means for obtaining the sum of the width of the ANEX signal pulses corresponding to one particle (e.g. counter, not shown), and arithmetic means for dividing the above data by 2, whereby the width data in a direction vertical to the moving direction is obtained.

The apparatus further comprises two signal processing means 244, 246 for obtaining binary signals by two different threshold data Th1, Th2, obtaining the binary signal S2(i) for detecting the entire particle and the binary signal S4(i) for detecting the nucleus portion of the particle, and obtaining AND signals S3(i), S5(i) by a logical AND operation between binary signals S2(i), S4(i) of scan cycle (i), and binary signals S2(i−1), S4(i−1) of one scan cycle before (i−1), corresponding to these two types of signals, and means for calculating the sum of the widths of the AND signal pulses corresponding to one particle as the particle area data and nucleus area data (e.g. counters CNT1, CNT2), and arithmetic means for dividing the nucleus area data by the particle area data (e.g. lookup table LUT2), whereby the nucleus area rate data is obtained.

The apparatus further comprises arithmetic means for obtaining the cumulative sum of the portion of the nucleus of the individual particles of the correction data S1(i), thereby obtaining the absorption quantity data of the nucleus portion.

The apparatus further comprises differentiating means 245 for obtaining the difference of the adjacent data on the time axis of the corrected data S1(i), means for calculating the sum of the differential data of the portion corresponding to one particle, or the sum of the square of the differential data as the complicated quantity data (e.g. accumulator, not shown), and arithmetic means for dividing the complicated quantity data by the area data from the arithmetic means (e.g. lookup table LUT1) (e.g. lookup table, not shown), thereby obtaining the complicated degree (complexity) data per unit area.

The apparatus further comprises arithmetic means (e.g. lookup table LUT4) for squaring the circumferential length data from the arithmetic means for calculating the circumferential length (e.g. accumulator and dividing by the area data from the arithmetic means for calculating the area (e.g. lookup table), thereby obtaining roundness (round shape degree) data.

The apparatuses further comprise plural sets of arithmetic means so that feature parameters of particles may be calculated simultaneously if plural particles simultaneously cross the imaging area of the one-dimensional image sensor. The arithmetic means (e.g. accumulator, not shown) is designed to function, when calculating the cumulative sum of the corrected data S1(i), only while the corrected data S1(i) is indicating a portion of the nucleus (the period in which the data exceeds the threshold level Th2 in FIG. 18).

A diluted and stained (dyed) specimen is led into a flat sheath flow cell 216, and a sheath liquid is supplied to form a flat sheath flow. The light from the light source 210 is emitted to the flat sample flow, and when the particle to be analyzed crosses this light emitting area, the exposure to the line sensor 222 is weakened.

Consequently, the image of the light transmitted through the particle to be analyzed is focused on the surface of the line sensor 222, and the signals corresponding to the exposure quantity for each picture element of the line sensor 222 are generated sequentially.

The detected signal by the line sensor 222 is subjected to signal processing, background correction processing, binarizing processing, binary signal processing, particle region division processing, arithmetic operation, etc., and the data is analyzed, and the absorption quantity information, morphological information and others of each particle are obtained in real time.

Embodiment 1

FIG. 2 shows Embodiment 1 of a particle analyzer. This apparatus is based on the conventional flow cytometer, and is combined with a detection system by a one-dimensional image sensor 22 (hereinafter called line sensor 22), and its signal processing means 24 (hereinafter called signal processing device 24).

A stained (dyed) specimen is led into a flow cell 14 composed of a transparent body of glass, plastic or the like, and a sheath liquid is supplied in such a manner as to cover the surrounding of the specimen, so that a flat sheath flow is formed. The laser beam from the laser source 10 is reduced by a cylindrical lens 12 so as to be thin in the particle flowing direction (the surface-reverse direction of the sheet in FIG. 2), and broad in the direction at right angles to the particle flowing direction (the up-down direction in FIG. 2), and is emitted to a specimen flow 16. When the particle in the specimen flow 16 to be analyzed crosses this laser beam, the exposure to the line sensor 22 is weakened. That is, the image of the light passing through the particle is focused on the surface of the line sensor 22 through objective lens 18 and projection lens 20, and signals corresponding to the exposure quantity for individual picture elements of the line sensor 22 are sequentially generated.

The time required for generating signals for all picture elements is determined by the number of picture elements and the clock frequency for shifting signals of all elements of the line sensor, and in the case of, for example, 256 picture elements and a clock frequency of 12 MHz, it takes about 20 µsec. This time is the time required for scanning the transmission images for one line, that is, the scan cycle.

Figure 3:
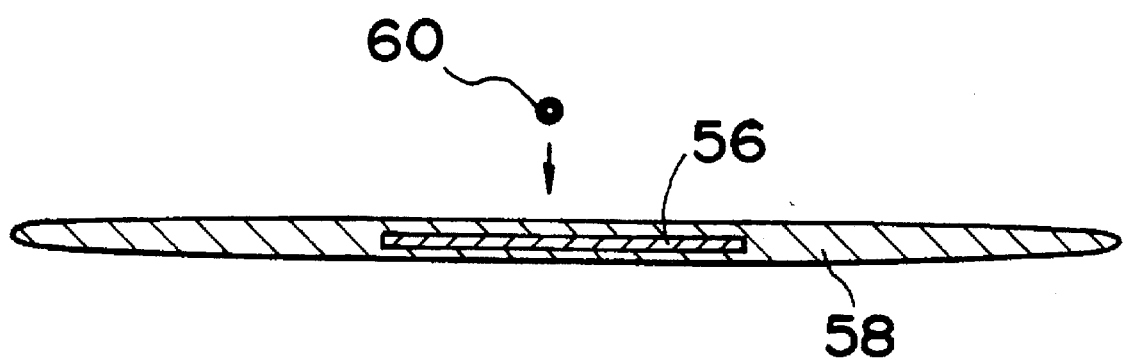
FIG. 3 is an explanatory diagram showing the beam emitting area and imaging area of a one-dimensional image sensor (line sensor) in FIG. 2.

FIG. 3 is a magnified view of the specimen liquid flow portion as seen from the direction of arrow A in FIG. 2. As shown in FIG. 3, in relation to the laser beam emission area 58, the line sensor imaging area 56 is located almost in the center of the emission area 58. Numeral 60 denotes a particle.

Figure 4:
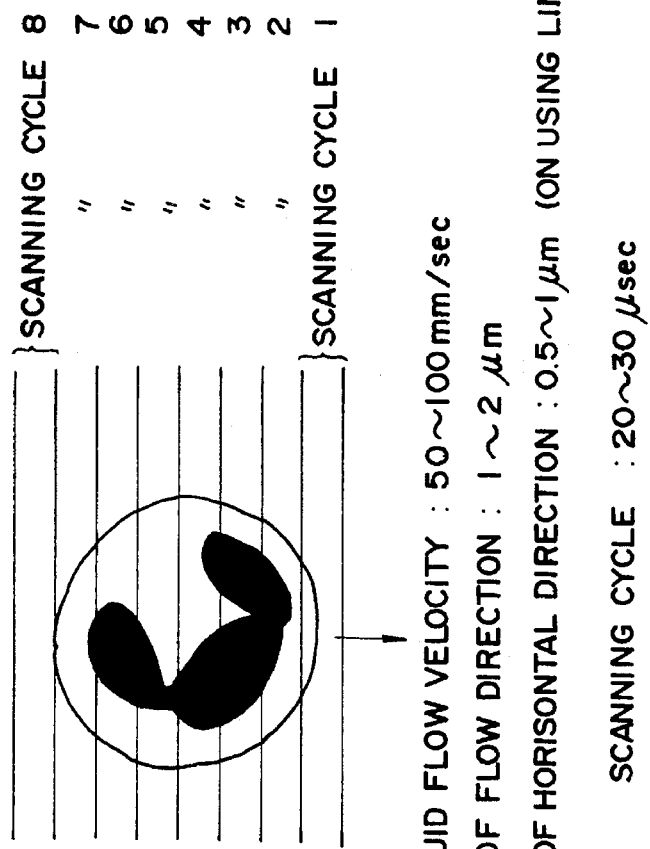
FIG. 4 is an explanatory diagram showing the state of particle scanning by a line sensor.
Figure 5:
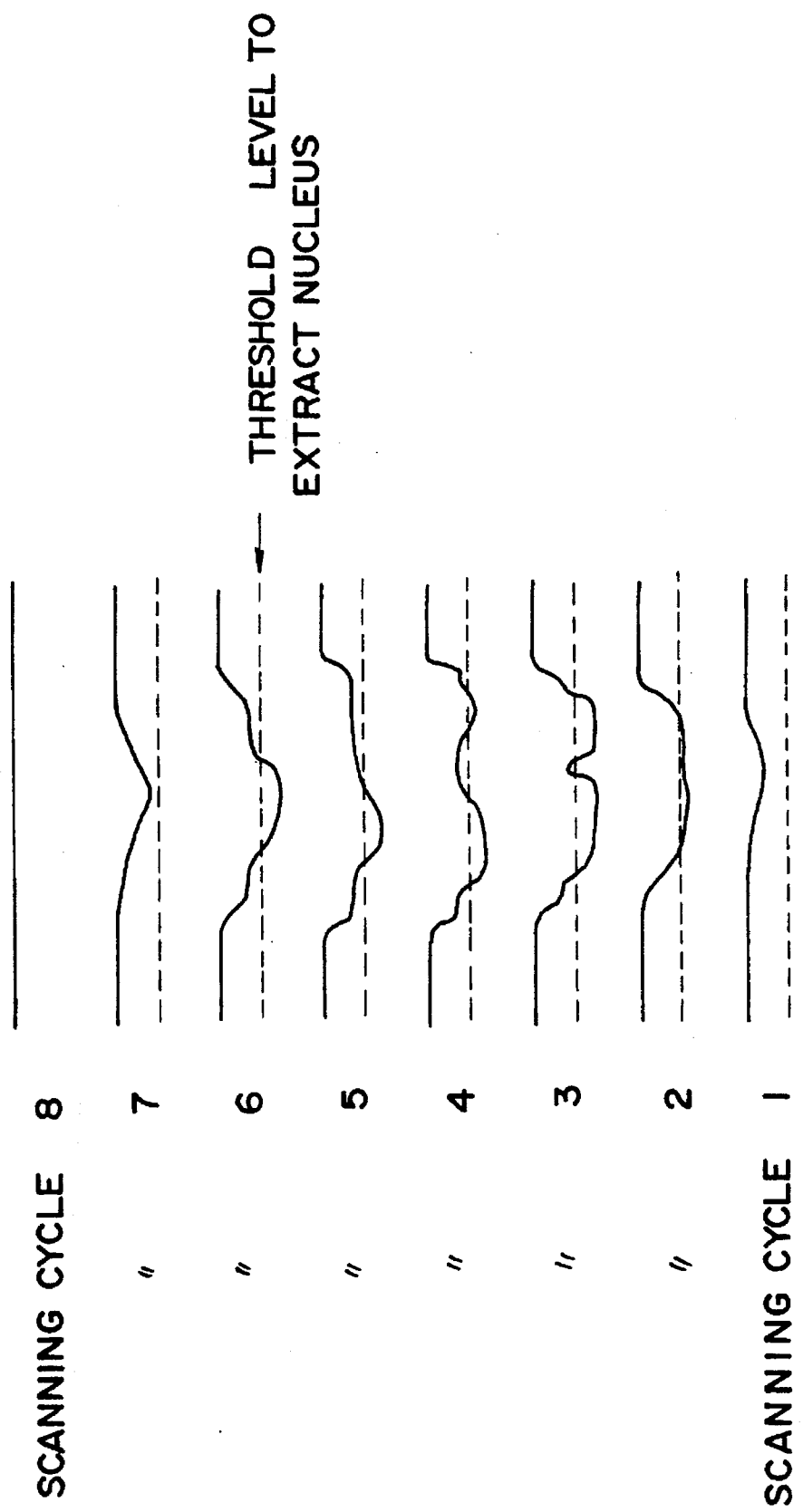
FIG. 5 is an explanatory diagram showing an example of a line sensor detection signal waveform, in which the broken line indicates the threshold level for extracting the nucleus.

The state of particle scanning by the line sensor 22 is shown in FIG. 4, and the detected signal waveform of the line sensor 22 in FIG. 5. By processing this detected signal, the morphological information and absorption information of the particle are obtained. The morphological information includes parameters, such as area of cell, circumferential length, area of nucleus (rate), circumferential length, width of cell, complicated degree inside cell (complicated quantity/area), and roundness. The absorption information includes parameters, such as absorption quantity, absorbance (absorbtive degree) (absorption quantity/area).

In addition to such parameters of morphological information and absorption information, by using the signals detected by the photo detectors 34, 32, further information, such as fluorescent intensity or side scattered light intensity is obtainable. The particle may be analyzed at a higher precision by using this information. Numeral 26 is an objective lens, and 28, 30 are dichroic mirrors.

In the apparatus of the present invention, however, the sheath flow velocity is limited to around 100 mm/sec. due to the relation with the scanning cycle and image resolution in the particle flowing direction, this flow velocity is about scores of times slower as compared with the conventional flow cytometer, and it is feared that the number of cells analyzed per unit time may be smaller.

To avoid this problem as far as possible, it may be considered to flatten the sample liquid in the flow cell 14 to increase the volume of sample flowing in the detecting part in unit time. For example, as compared with a conventional round sheath of 15 μm in diameter (columnar sheath), a flat sheath of 15×150 μm is used, and sample volume per unit time is increased about 13 times at the same flow velocity. However, if the concentration of particles to be analyzed is high, the possibility of simultaneous passing of plural particles in the detecting part increases. And it is necessary to extend the width of the laser beam for emitting the detecting part, which results in lower emission intensity, and therefore the following counter-measures may be considered in a system required to capture feeble fluorescence.

(1) To raise the laser power.

(2) To reduce the laser emission width in the direction of particle flow.

(3) To use a high sensitive photomultiplier.

Figure 7:
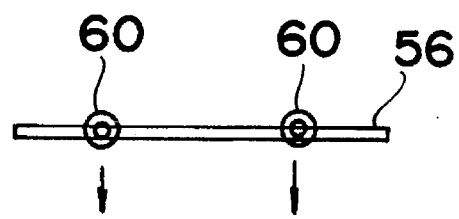
FIG. 7 is an explanatory diagram showing the state of two particles crossing the line sensor simultaneously.
Figure 8:
FIG. 8 is an explanatory diagram showing an example of the detection signal waveform in FIG. 7.

Concerning the increase of the simultaneous passing rate by flattening the specimen flow, if the simultaneous passing rate in the case of a round sheath is 0.5%, that of the flat sheath is 5%, for example. When two or more particles pass simultaneously side by side as shown in FIG. 7, in the slender detecting area (imaging area) 56, the signal value of the scatter intensity or fluorescence intensity obtained in the detecting system of the conventional flow cytometer does not correspond to one particle. Besides, it is difficult to judge from the signal waveform whether the particles have passed simultaneously or not. On the other hand, the detected signal by the line sensor 22 is as shown in FIG. 8, and from this detected signal waveform it is easy to judge whether particles pass simultaneously or not.

On the basis of the result of a judgement, it may be controlled to ignore the optical information obtained in the case of a simultaneous passing. By flattening the specimen flow, the simultaneous passing rate increases to 5%, and if such particles are ignored, the substantial increasing effect of the quantity of the sample to be analyzed is still great. In addition, by flattening the flow of liquid specimen, it is also effective to align the flat cell orientation hydrodynamically.

Concerning the flattening of the liquid specimen, a further consideration is required in the sectional shape of the flow cell. The conventional flow cell for flat sheath is flat as disclosed in the U.S. Pat. No. 4,338,024 or Japanese Patent Publication Sho. 57-500995, but in this shape it is impossible to obtain the side fluorescence or side scattered light detected by the conventional flow cytometer. Accordingly, it gives rise to the necessity of a flow cell for a flat sheath that is not too flat. That is, in the conventional flow cell of large slender ratio (the vertical size is much larger than the lateral size, for example, scores of times, and a degree of flatness is large), the side light signal cannot be detected, and therefore the flow cell of a small slender ratio (the vertical size is somewhat larger than the lateral size, for example, one to several times, and the degree of flatness is small) is needed. An apparatus for forming such a flat sheath flow is disclosed in Japanese Patent Applications Hei. 3-210053 and Hei. 3-210054. The apparatus gradually narrows only the width of one direction of the passage for flow cell inlet, opening the discharge port of the sample nozzle flatly, and matching the shorter direction of the discharge port with the decreasing direction of the inlet passage. The apparatus disposes sheath liquid dividing means for dividing symmetrically the sheath liquid into two flows in contact with the sample nozzle, and positions the discharge port of the sample nozzle in the sheath liquid converging region downstream of the sheath liquid dividing means.

Instead of forming a round sheath flow by using the flow cell 14 shown in FIG. 2, a flat sheath flow may be formed by using the flat sheath flow cell 15 as shown in FIG. 9, so that the capacity to analyze per unit time may be increased.

Embodiment 2

FIG. 9 shows Embodiment 2 of a particle analyzer. This apparatus is based on the apparatus of Embodiment 1, and combined with a second light source 36 such as a strobe light source (hereinafter called strobe light source 36) for obtaining further particle images, an imaging system including second capturing means 38 such as a video camera (hereinafter called video camera 38), and an image processing device 40. Numeral 37 is a power source for the strobe. That is, on the basis of the optical information and morphological information obtained in the apparatus of Embodiment 1, each particle is analyzed in real time, and when the particle is judged to be the particle to be observed closely, the strobe light source 36 is triggered, and the flowing particle is illuminated instantly, and the particle image is captured by the video camera 38.

The light from the strobe light source 36 is transformed into parallel light by a collimator lens 42, and only the light excluding the light of the waveform below the near ultraviolet rays is reflected by the mirror 44, and is emitted to the imaging area of the video camera 38 through the lens 46. The light transmitting through the particle is reflected by the mirror 48 through the objective lens 18, and is focused on the CCD plane of the video camera 38.

When strobe light is emitted at this time, in order that the side fluorescence or side scattered light by this light may not be detected, it is desired to use a photomultiplier with a gate function as the photo detectors 52, 50. That is, for the period of 1 or 2 μsec. of illumination of the strobe light, the gate is applied so that the photomultiplier may not function, or it is exempted from the object of signal processing during the strobe illumination period. Numeral 25 is a signal processing device, and 47 is a projection lens.

Figure 10:
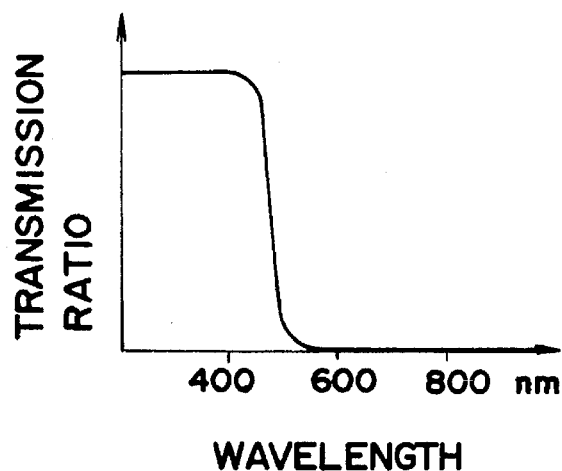
FIG. 10 is a diagram showing an example of a characteristic diagram of a dichroic mirror.

The wavelength of the laser beam always emitted from the laser light source 10 is, for example, 441.6 nm in the case of a helium-cadmium laser, and by using the dichroic mirrors 44, 48 which pass the light of this wavelength (441.6 nm), but do not pass the light more than this wavelength, the laser beam and the light for the video camera imaging are separated. Since this wavelength is the wavelength at the end of the visible light region, the color image of a particle may be captured in a sufficient satisfactory color quality (tone of color). A characteristic example of the dichroic mirror is shown in FIG. 10.

Figure 11:
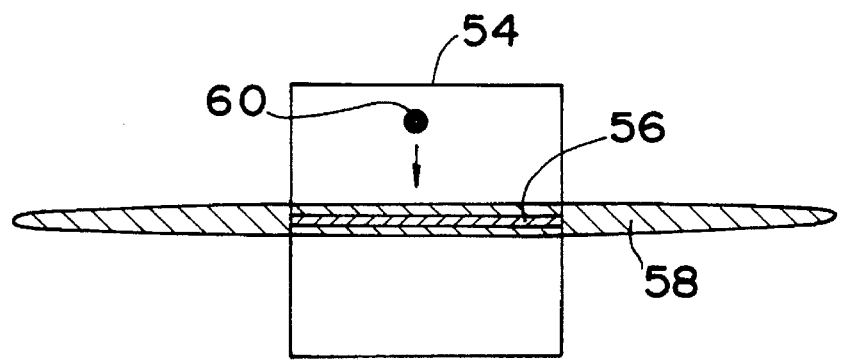
FIG. 11 is an explanatory diagram showing the laser beam emitting area, imaging area of a line sensor, and imaging area of a video camera in FIG. 9.

The relation between the imaging area of the line sensor and the imaging area of the video camera in the embodiment is shown in FIG. 11. As shown in the diagram, the imaging area 56 of the line sensor and the imaging area 58 of the laser beam are located nearly in the center of the imaging area 54 of the video camera, and the imaging system by the video camera 38 may be added to the same optical axis system as the optical axis system in Embodiment 1, so that the optical system may be constructed in a compact form. This is possible because the detected signal processing of the line sensor is done in real time, the parameters of morphological information and absorption quantity are obtained within 100 μsec. after the particle 60 crosses the imaging area 56 of the line sensor, and the type of the particle can be judged on the basis of these parameters, fluorescence intensity, and/or side scattered light intensity, and in the case of a sheath flow velocity of 100 mm/sec., the particle moves only 10 μm in 100 μsec. Meanwhile, for the detecting part, as the flow cytometer and the imaging area of the video camera are apart from each other, a delicate control is required for the stability of the sheath flow velocity and the timing of the capturing image.

Figure 12:
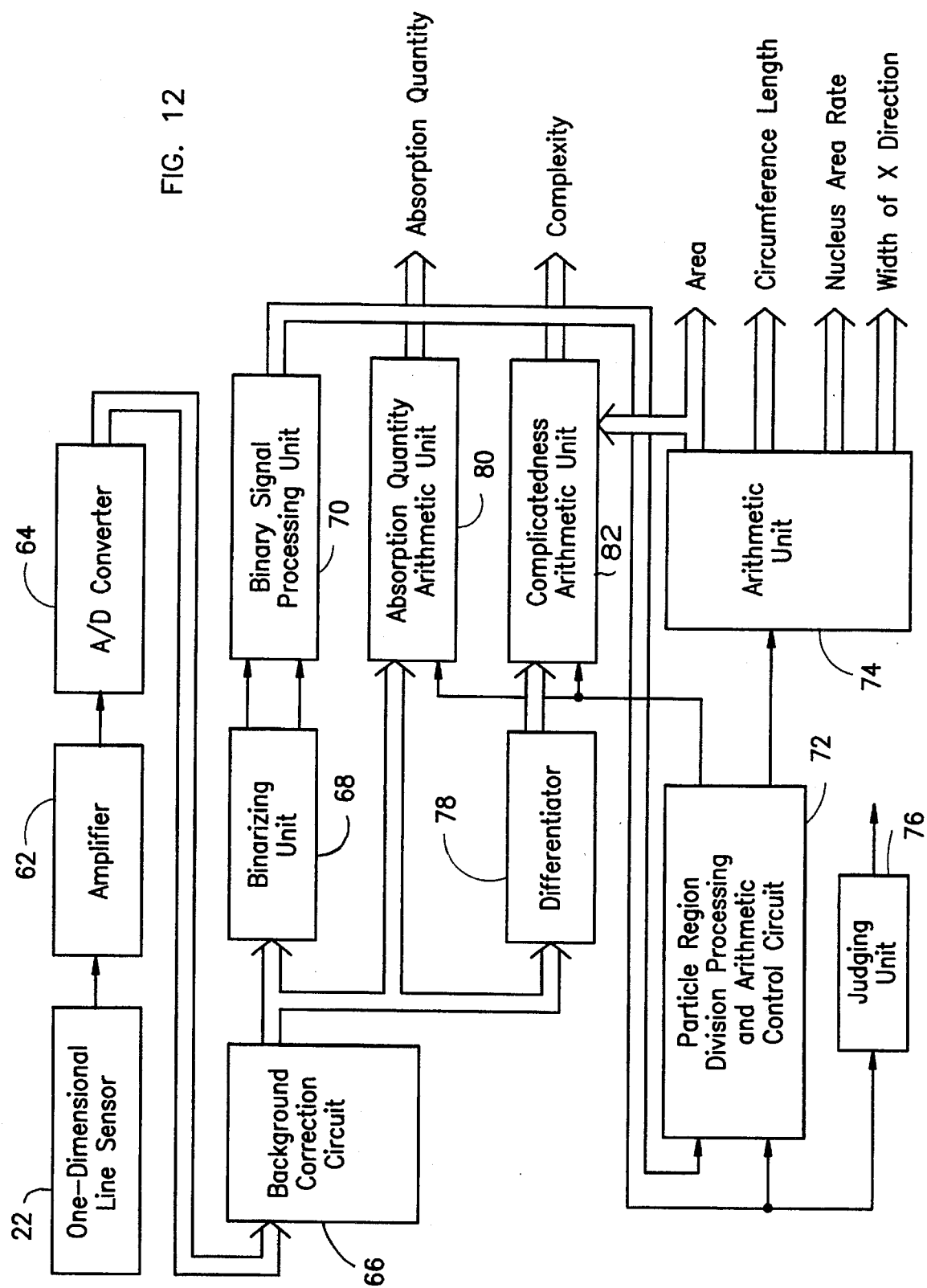
FIG. 12 is a block diagram showing an example of a signal processor for the detected signal by the line sensor.

Given below is the outline about the processing of the detected signal by the line sensor 22 in Embodiment 1 and Embodiment 2. An example of a detected signal waveform obtained by the line sensor is shown in FIG. 5. An example of a block diagram of a signal processing circuit for processing such a signal and obtaining the morphological information and absorption information of the particle is shown in FIG. 12.

The signal from the line sensor 22 is amplified by the amplifier 62, and is A/D converted by the A/D converter 64 in the sampling clock at the same frequency as the shift clock of the line sensor, and the data is corrected and processed in the background correction circuit 66. In the background correction circuit 66, the background data of one scanning cycle obtained when the particle is not passing through the detecting part is preliminarily stored in memory, and the difference between the background data and the A/D converted data obtained during measurement is obtained and led out, all by real time processing. It is the object of this processing to correct the shading of the laser beam emission and fluctuations of sensitivity of each picture element of the line sensor.

Figure 6:
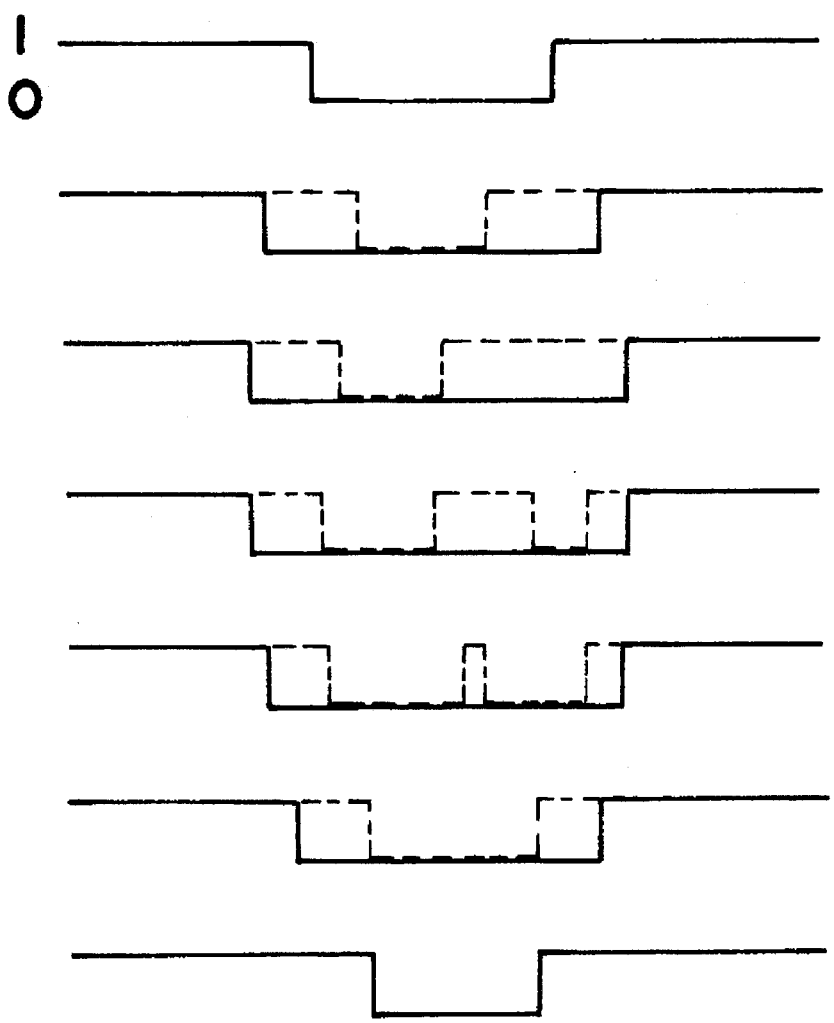
FIG. 6 is an explanatory diagram showing an example of logic waveforms after binarizing for the waveform shown in FIG. 5, in which the broken line indicates the binarized signal by threshold level for extracting the nucleus portion.

The corrected data is compared with data of a certain proper reference level in order to cut out the portion corresponding to the transmitted light image of the particle, and is binarized in the binarizing unit 68. Furthermore, in order to cut out only the portion of the nucleus stained (dyed) at high density, the data is also compared with the data of larger level than the reference level, and is binarized. An example of a binarized signal waveform is shown in FIG. 6.

The binarized signal is pretreated in the binary signal processing unit 70 in order to remove small debris and divide the region of binary signal corresponding to individual particles. The particle region division processing in this case is to cut out the region (timing) of the binary signal corresponding to one particle appearing in plural continuous line data, and this processing is necessary for creating the timing control signal for calculating the morphological information or absorption information of individual particles in real time.

The arithmetic unit 74 for obtaining the absorption quantity, complicatedness and morphological information is controlled by the control signal from this particle region division processing and arithmetic control circuit 72, and the parameters for individual particles may be calculated in real time.

From the binary signal processed signals, simultaneous passing of particles is judged in the simultaneous passing judging unit 76, and it may be controlled so as to ignore the parameters obtained in this case. Numeral 78 is a differentiator, 80 is an absorption quantity arithmetic unit, and 82 is a complicatedness arithmetic unit. The complicatedness is calculated by summing up the differences of A/D converted adjacent data within a range corresponding to one particle (complicated quantity), and dividing it by the area. As the complicated quantity, meanwhile, the squares of the differences of adjacent data may be summed up in a range corresponding to one particle.

The present invention illustrated in FIG. 2 through FIG. 12 brings about the following effects.

(1) In addition to the optical features of the particles obtained in the conventional flow cytometer (scattered light intensity, fluorescence intensity, etc.), the morphological information of particles may be obtained in real time, and a particle analysis in higher precision is realized. Besides, since the specimen is formed in a flat sheath flow and measured, the possibility of two or more particles passing side by side to cross the monitoring area of the line sensor increases, but by processing the detected signal of the line sensor, this state can be judged, and therefore it is possible to control so as to ignore the fluorescence signal and scattered light signal obtained as in the conventional flow cytometer, as the signals of simultaneous passing of particles (the sample width may be increased, and the number of particles that are analyzed may be increased).

(2) Since the sample flow including the particles is flat, when the strobe light source and video camera are added, only the particles that must be inspected particularly in detail among many types of particles can be sorted with high precision and image-captured. Besides, by high speed signal processing of the detected signal by the line sensor, the morphological information of particles can be obtained in real time, and therefore the capturing area of the video camera may contain the detection area as the flow cytometer and the detection area of the line sensor, so that the optical system may be formed in a compact design. It is not necessary to consider the deviation of the timing caused by division of the imaging area as in the prior art, and it is possible to capture particle image securely in spite of changes in flow velocity.

(3) The expensive polarizer element and its driver circuit required in the conventional system are not needed.

(4) When the apparatus of the present invention is applied in the conventional cell sorter, by adding the particle morphological information and absorption quantity or absorbance, in addition to the optical information obtained by the prior art, as the information for making a sorting judgement, the particles may be separated in higher precision.

Embodiment 3

FIG. 13 shows Embodiment 3. The specimen including the particles to be analyzed is led into a sheath flow cell 216 and a flat liquid specimen flow 217 is formed. That is, it flows in the flow cell 216 as a flat specimen flow thin in the direction of the optical axis, and broad in the direction at right angles to the optical axis. The specimen flows in a direction vertical to the sheet of paper in FIG. 13. The flow cell 216 is formed of a transparent body such as glass or plastic.

The light from the light source 210 is transformed into parallel light by a collimator lens 212, is reduced into a slender form by a cylindrical lens 214, and is emitted to the specimen flow region of the flow cell 216.

As the flow cell, a flat shape as disclosed in U.S. Pat. No. 4,338,024 or Japanese Patent Publication Sho. 57-500995 may be used. But with these flow cells the side light signal cannot be detected because the slender ratio of the flow cell is too large (the vertical size is too large for the lateral side, for example, scores of times, and the flatness is large). Accordingly, a flow cell of small slender ratio is required (the vertical size is slightly larger than the lateral side, for example, one to several times, and the flatness is small). As the apparatus for forming such a flat sheath flow, that shown in Japanese Patent Applications Hei. 3-210053 and Hei. 3-210054 may be used. This apparatus gradually narrows only the width of one direction of the passage for flow cell inlet, opening the discharge port of the sample nozzle flatly, and matching the shorter direction of the discharge port with the decreasing direction of the inlet passage. Also, the apparatus for disposing sheath liquid dividing means for dividing symmetrically the sheath liquid into two flows in contact with the sample nozzle, and positioning the discharge port of the sample nozzle in the sheath liquid converging region downstream of the sheath liquid dividing means is disclosed therein.

Therefore, as the flow cell 216 shown in FIG. 13, it is preferred to use the flow cell with the small slender ratio.

FIG. 14 is a magnified view of the portion of the liquid specimen flow 228 as seen from the direction of arrow B in FIG. 13. The light 232 reduced into a slender elliptical form is emitted to the line sensor detection area 234. The light from the line sensor detection area 234 is focused on the light receiving plane of the one-dimensional image sensor 222 (hereinafter called the line sensor 222) by the objective lens 218 and projection lens 220. In FIG. 14, W1 denotes the width of the liquid specimen flow, and W2 is the width of the detection area 234 of the line sensor.

The detected signal by the line sensor 222 while the particle 230 has not crossed the detection area 234 of the line sensor is signal Sa as shown in FIG. 15 (a). The signal waveform at this time should be ideally a flat straight line, but actually the signal waveform is undulated due to sensitivity fluctuations of picture elements of the line sensor, or shading of light illumination in the longitudinal direction of the detection area of the line sensor.

Figure 16:
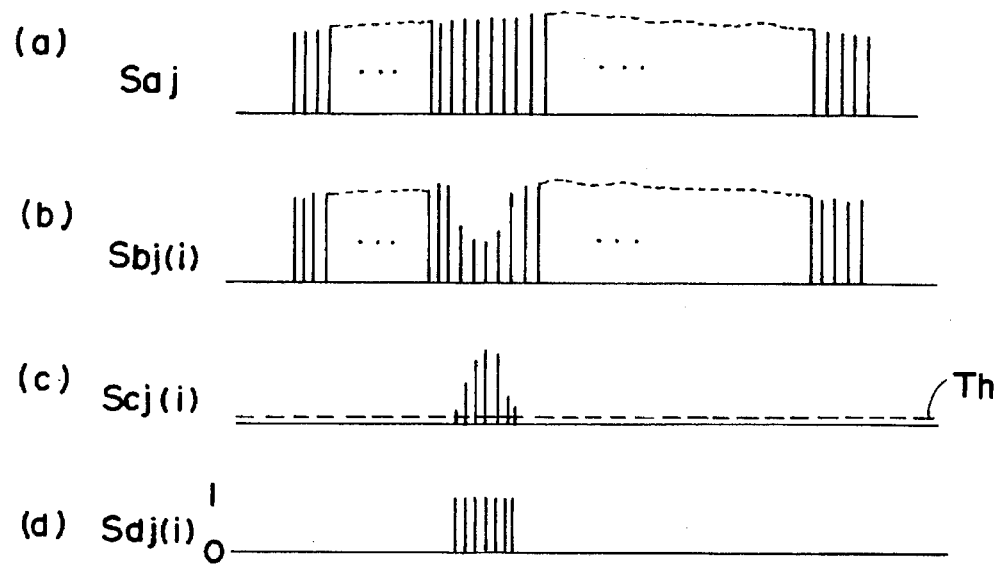
FIG. 16 is an example of a waveform diagram by signal processing for the detected signal by the line sensor.

In a certain scan cycle (i), while the particle 230 is crossing the detection area 234 of the line sensor, the light is blocked (weakened) by the particle, and therefore the image signal Sb(i) as shown in FIG. 15 (b) is obtained. By subtracting the signal Sb(i) from the signal Sa, as shown in FIG. 15 (c), the signal Sc(i) being rid of the fluctuations of picture elements of the line sensor and effects of shading is obtained. This is called the background correction processing. Furthermore, by comparing the signal Sc(i) with the reference level Th, the binary signal Sd(i) indicating the presence of a particle is obtained as shown in FIG. 15 (d). In actual processing, this processing is done digitally. That is, just before a start of measurement, by converting signal Sa from analog to digital as shown in FIG. 16 (a) to (d), the waveform data Saj of the time series is obtained, and the data Saj is stored in memory, and similarly the difference between the data Saj and the time series waveform data Sbj(i) of the signal Sb(i) obtained after start of a measurement is calculated digitally in real time to determine Scj(i). This background corrected data Scj(i) is compared with proper reference data (threshold level) Th1, in order to extract only the portion of the particle, thereby obtaining binary data Sdj(i).

Explained next is how to obtain the information such as absorption information and morphological information in real time from the detected signals by the line sensor.

Figure 17:
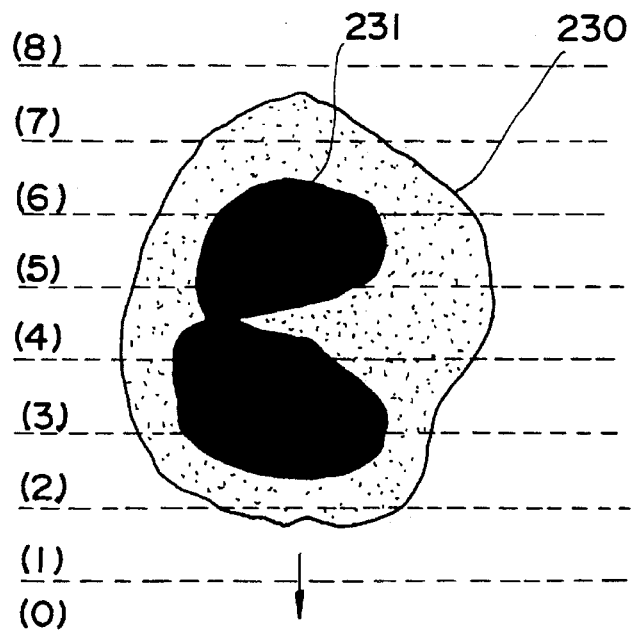
FIG. 17 is an explanatory diagram showing the state of particle scanning by the line sensor.
Figure 18:
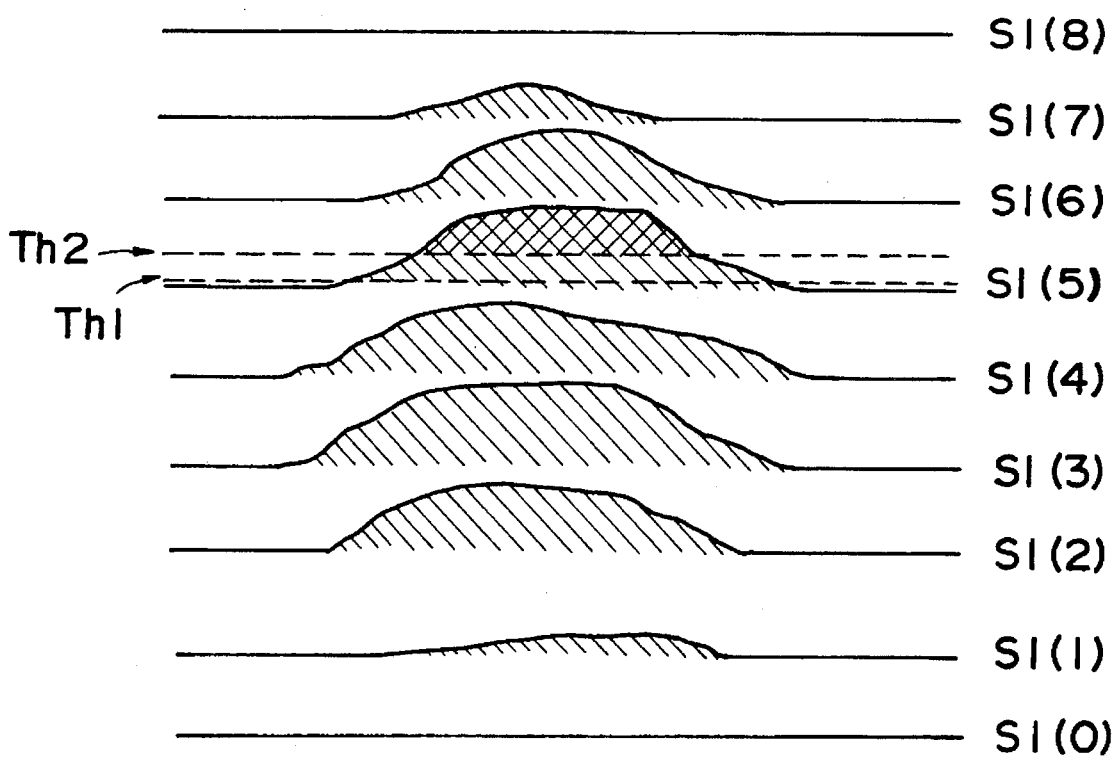
FIG. 18 is an example of a waveform diagram of background corrected signals in every scanning cycle.

FIG. 17 shows a scanning state for a certain particle 230 by the line sensor. Numeral 231 is a nucleus. The figures in parentheses in FIG. 17 denote the scan cycle (i). At this time, the signal obtained in each scan cycle (i) is subjected to the above background correction, and the data S1(i) shown in FIG. 18 is obtained. The value summing up the area of the shaded portion in FIG. 18 is equivalent to the absorption quantity of the particle. The absorption quantity may be divided by the particle area to obtain the absorbance.

Meanwhile, the threshold levels Th1, Th2 in FIG. 18 are levels for extracting the whole particle and the nucleus of the particle, respectively. By summing up the area (indicated by shaded zone) of the portion where the data S1(i) is over the threshold level Th2, the absorption quantity of the nucleus portion may be obtained. When the nucleus is stained (dyed) in Feulgen's method, the absorption quantity and the DNA quantity are in satisfactory correlation, so that useful information is obtained.

Figure 19:
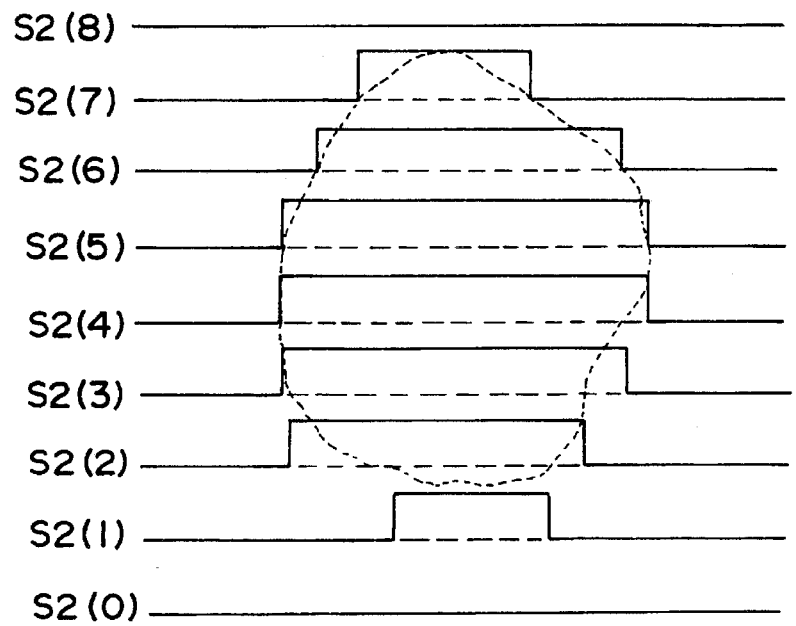
FIG. 19 is an example of a logic waveform diagram by binarizing for the signal shown in FIG. 18 by threshold level Th1.
Figure 20:
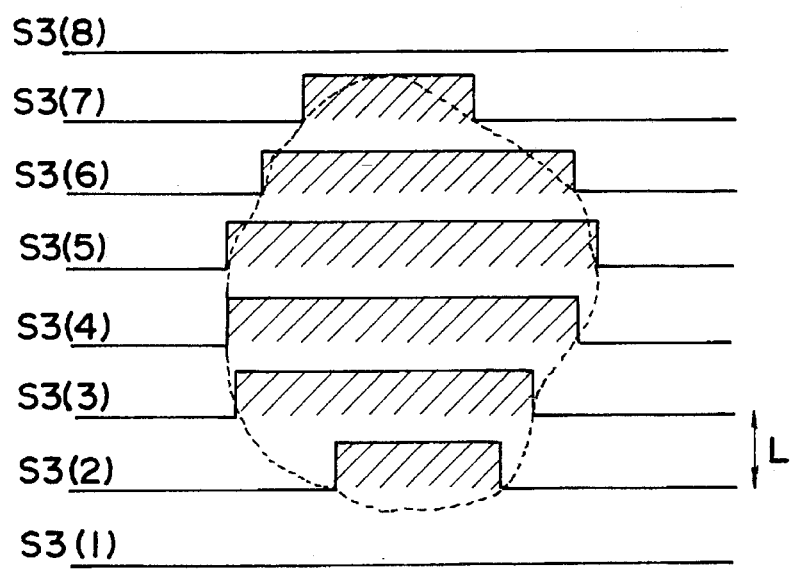
FIG. 20 is an example of a waveform diagram after an AND operation for the signal in FIG. 19.

FIG. 19 shows the logic signal S2(i) when the signal shown in FIG. 18 is binarized by threshold level Th1 for particle extraction. The area of the particle is obtained by using this signal, but when the periods of high levels of binary signals are summed up directly, the result is a little larger than the area of the actual particle. Accordingly, as shown in FIG. 20, the AND operated signal S3(i) between the binary signal S2(i−1) obtained in scan cycle (i−1) and the binary signal S2(i) obtained in the present scan cycle (i) is obtained sequentially, that is, S2(i−1)×S2(i), and it is known that the value is closer to the actual value of the particle area by summing up the high level periods of these binary signals S3(i). Actually, the sum value is multiplied by the distance data L of the particle moving in one scan cycle to obtain the area.

Figure 21:
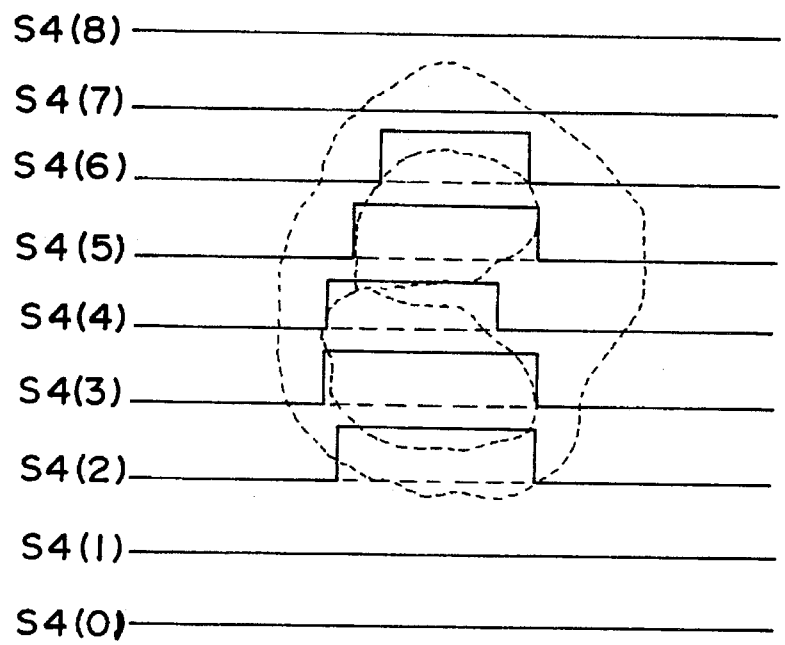
FIG. 21 is an example of a logic waveform diagram by binarizing for the signal shown in FIG. 18 by threshold level Th2.
Figure 22:
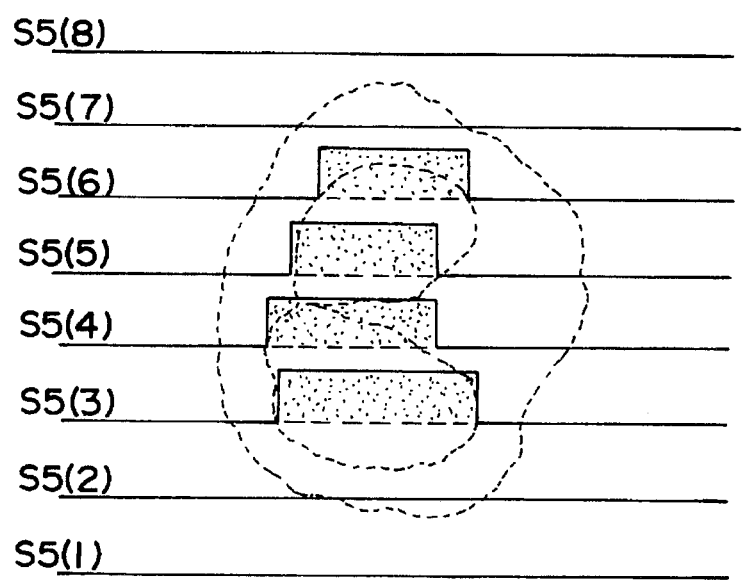
FIG. 22 is an example of a waveform diagram after an AND operation for the signal in FIG. 21.

If the particle to be analyzed has a nucleus inside, such as a leukocyte, the threshold level Th2 for extracting only that nucleus portion is set separately, and by processing the binarized signal in comparison with the level, the area of the nucleus portion may be obtained similarly (see FIGS. 21, 22).

Figure 23:
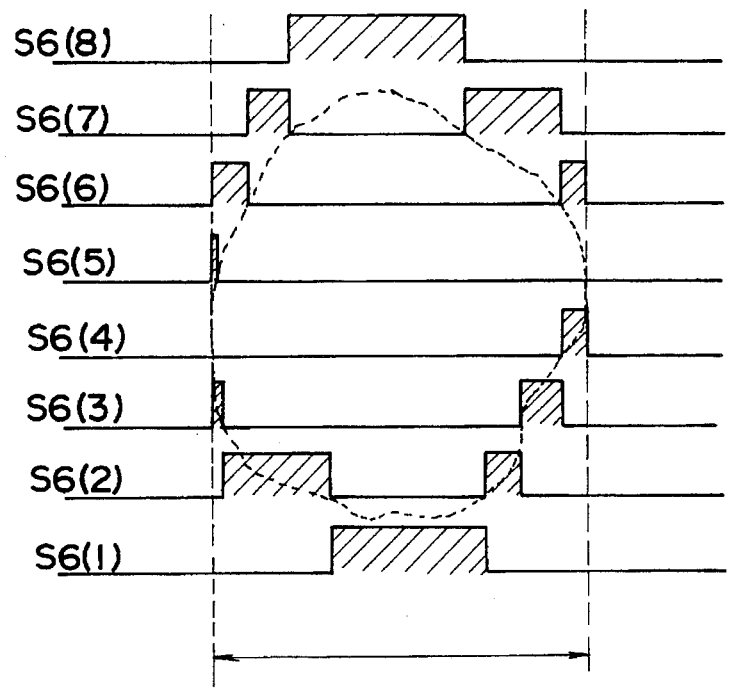
FIG. 23 is an example of a waveform diagram obtained by an exclusive-or operation for the signal shown in FIG. 19.

The method of calculating the approximate value of the particle width and circumferential length is explained below. The exclusive-or operated signal (EXOR) S6(i) between the binary signal S2(i−1) obtained by the scan cycle (i−1) and the binary signal S2(i) obtained in the present scan cycle (i) is successively obtained, as shown in FIG. 23. The value obtained by summing up the high level periods of this signal is almost equivalent to twice the width in the direction vertical to the moving direction of the particle (X-direction). Accordingly, half of the value may be regarded as the particle width in the X-direction. Meanwhile, S6(i) is determined by the following Formula, $$S6(i)=S2(i-1)\oplus S2(i)\geq S2(i-1)*\overline{S2(i)}+\overline{S2(i-1)}*S2(i)$$

Figure 24:
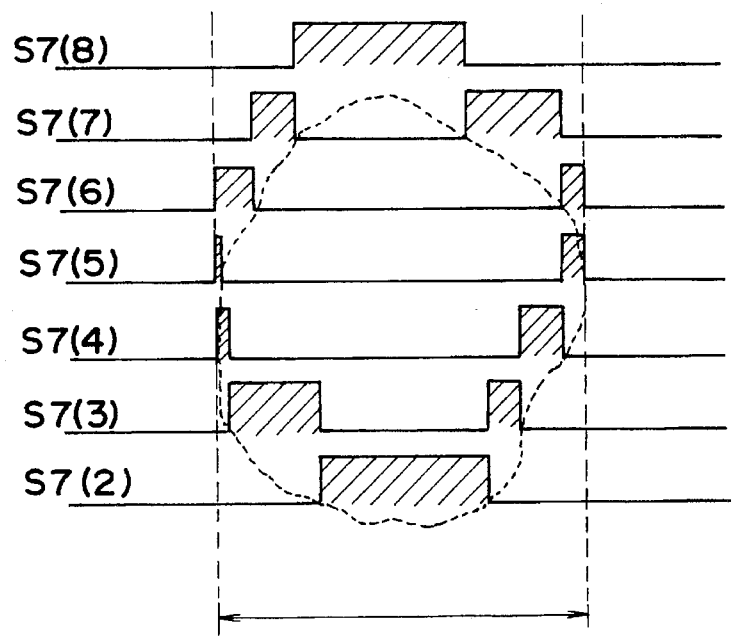
FIG. 24 is an example of a waveform diagram obtained by an exclusive-or operation for the signal shown in FIG. 20.

Besides, from this FIG. 23, the approximate value of the circumferential length of the particle is obtained by summing up the square root of the addition of the square of each EXOR signal pulse and the square of the particle moving extent in one scanning cycle. The accuracy is higher when the number of scanning times for one particle is greater or the moving distance of the particle in one scan cycle is shorter. FIG. 24 shows an example of an ANEX waveform of exclusive-or operated signals S7(i) between adjacent scan cycles of the AND signal shown in FIG. 20. A method of calculating the width and circumferential length of particle by using those signal S7(i) is similar.

From the thus obtained value, the roundness and area rate of the nucleus can be also calculated. As to the roundness, generally, the squared value of the circumferential length divided by the area is widely used. This value is the smallest in the case of a circle, and is larger as the shape of the particle is slender, and if the shape is identical, the value is the same regardless of the size.

As to other parameters obtained by processing the detected signal by the line sensor, it may be also considered to express the value obtained by differentiating the detected signal, adding the value and dividing by the area as the complicatedness inside the particle.

Figure 25:
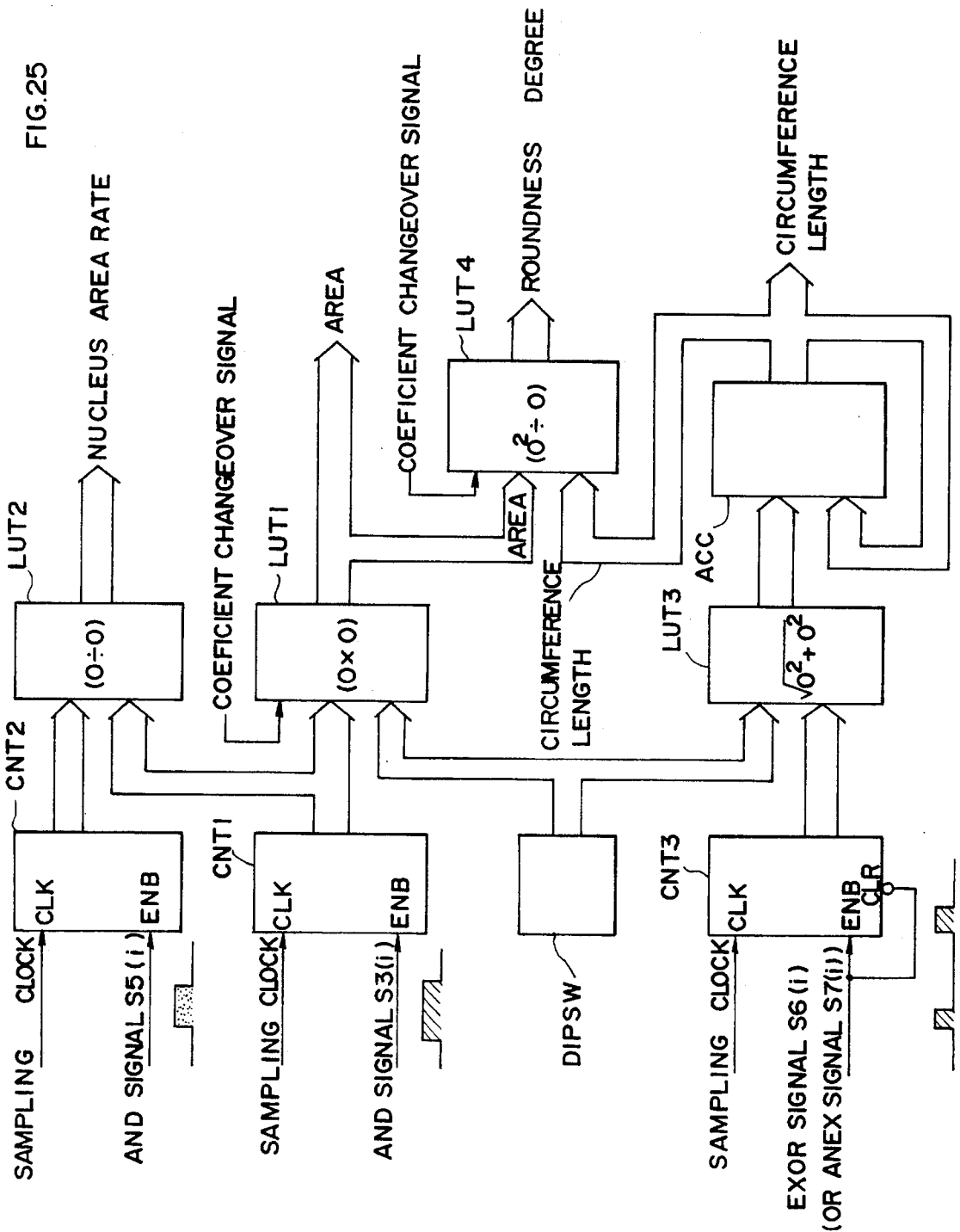
FIG. 25 is a block diagram showing an example of a calculating circuit for obtaining parameters in real time.

As an example of an arithmetic circuit for calculating the above parameters actually in real time, an example of an arithmetic circuit for calculating the area, circumferential length, roundness and nucleus area rate is shown in FIG. 25.

When the AND signal S3(i) expressing the portion of the particle (FIG. 20) is high, the counter CNT1 counts the number of sampling clock pulses, and when the width of all AND signals S3(i) corresponding to one particle is counted, the value is entered in the lookup table LUT1. In this lookup table LUT1, the value corresponding to the particle moving extent L predetermined by the dip switch DIPSW is also entered, and when the two sets of data are input, the multiplied value is output from the LUT1 within 150 nsec. The coefficient changeover signal entered in the lookup table LUT1 is changed over depending on the magnitude (size) of the particle to be analyzed. This is intended to suppress the data of wide dynamic range by the size of particle to the data in the number of bits easy to handle by the data analyzer.

Likewise, the width of all AND signals S5(i) corresponding to the nucleus portion of one particle is counted by the counter CTN2, and the value is entered in the lookup table LUT2. In the LUT2, the data from the counter CNT1 is also entered, and the rate of the area of the nucleus portion corresponding to the area of the entire particle is output from the LUT2.

On the other hand, when the EXOR signal S6(i) or S7(i) becomes high, the counter CTN3 begins to count, and when the signal changed from high to low, the result of counting is transferred to the lookup table LUT3, and the counter CNT3 is cleared. In the LUT3, the value corresponding to the particle moving distance in one scanning cycle is also entered from the dip switch DIPSW, and the data of the square root of the sum of the squares of these two pieces of input data is instantly output from the LUT3. The output data is added, by accumulator ACC, for every EXOR signal pulse. The value obtained by summing up all EXOR signal pulses of EXOR signal pulses corresponding to one particle is produced as approximate data of circumferential length.

Thus obtained circumferential length and area data are entered in the LUT4 and data of (circumferential length)$^2$/ area of the roundness is produced instantly from the LUT4.

The lookup table (LUT) herein refers to the result of a calculation which is written in memory beforehand as the numerical table, and it is the general means where real time arithmetic processing is required. The time from the input of the data till output of the data depends on the access time of the memory.

FIG. 26 is a block diagram of an embodiment of the entire processing circuit (signal processing means) 224 for processing the detected signals by the line sensor 222 and calculating the parameters. The detected signal by the camera 236 with the line sensor 222 is amplified, and is fed into the A/D converter 240 through a filter 238 for removing noise and high frequency components due to the shift clock of the line sensor or the like. The A/D conversion is effected in synchronism with the shift clock, and the data is transferred to a background correction processing circuit 242. This circuit 242 possesses a line memory for holding the data of one line (one scanning cycle) while the particle does not cross the line sensor detection area before start of measurement, and the difference from the data of each scan cycle after start of measurement iscalculated. Thus corrected data is binarized in the binarizing processing circuit 244 possessing two sets of reference data (threshold levels) Th1, Th2. The binarized data is sent to binary signal processing circuit 246 to be pretreated for calculating the area and circumferential length, that is, logical operation such as AND, exclusive-or operation between two lines (scanning cycles) of binary signal, and pretreatment for dividing (regional dividing) of the signal of the portion corresponding to one particle. The processed data is transferred to the regional division processing part 248 and arithmetic unit operation control circuit 250.

The regional division processing in this case is the processing to determine whether each binary signal pulse indicating the part of the particle belongs to which particle, and it appears in the continued plural lines (scanning cycles). It is intended to deliver the range of binary signals corresponding to one particle as one arithmetic control signal, and if two or more particles, close to each other, pass through the detection area of the line sensor, it is controlled to assign which set of arithmetic unit to which particle when plural sets of arithmetic units are installed so as not to overlook the particles.

I the arithmetic unit operation control unit 250, using the regional division signal and the signal from the binary signal processing unit, signals are created to control the operation of the arithmetic unit of each parameter. That is, when the binary signal, the AND signal, the EXOR signal or the ANEX signal is changed from low to high, it is controlled to start or continue the operation of each arithmetic unit, and when the signal is changed from high to low, a signal is produced for controlling to end or interrupt the operation of each arithmetic unit. Besides if two or more particles pass the detection area close to each other, when plural sets of arithmetic units are provided so as not to overlook the particles, it is controlled to change over the sets of the arithmetic unit to be operated for every signal corresponding to the particles. Besides, the control signal for obtaining the absorption quantity is also generated from the arithmetic unit operation control unit 250.

The absorption quantity arithmetic unit 252 is intended to sum up the data after background correction processing. The degree of complicatedness is obtained by calculating the difference of the adjacent data by the differentiator 245, summing up the difference data by the complicatedness arithmetic unit 254, and dividing the sum by the area. The morphological information arithmetic unit 256 is a circuit as shown in FIG. 25, for example. A counter circuit 258 is intended to count the particles detected by the line sensor.

In this way, the parameters obtained in real time by the signal processing device 224 every time the particle passes through the detection area of the line sensor are transferred to the data analyzer 226 (see FIG. 13), and the particles are analyzed and classified.

To obtain the particle width and circumferential length, it is explained above to get an EXOR signal between binary signals S2(i) and S2(i−1), but it is also possible to use an AND signal S3(i) between binary signals S2(i) and S2(i−1), and obtained from ANEX signal by EXOR-operation between the AND signals S3(i) and S3(i−1).

(1) When obtained by using the EXOR signal—to have EXOR between S2(i) and S2(i−1):

The X width is obtained accurately. The circumferential length tends to be longer than the real length by about twice the moving extent in one scanning cycle.

(2) When obtained by using an ANEX signal—to have EXOR between S3(i) and S3(i−1):

The X width tends to be smaller than real. The circumferential length tends to be slightly smaller than real.

It is not possible to decide which method is better. Anyway, the accuracy of the approximate value is higher when the moving distance of the cell in one scanning cycle is shorter.

As explained in FIG. 13 through FIG. 26, the present invention is thus constructed, and hence brings about the following effects.

(1) The approximate values of the absorption quantity and morphological information of moving particles may be obtained in real time without using an expensive video camera or image processing system.

(2) By adding the detection system by line sensor and signal processing device of the present invention to the conventional flow cytometer or cell sorter, novel feature parameters for individual cells are obtained, and it is possible to classify the particles in higher precision.

(3) By adding the detection system by line sensor and signal processing device of the present invention to the conventional imaging flow cytometer, only the particles of interest can be sorted out, and the desired particles may be efficiently captured by the video camera and edited.

(4) If the particle concentration of sample liquid is high, by installing plural sets of arithmetic units, up to about 10,000 particles per second may be analyzed in real time.

(5) By flattening the liquid specimen flow, the orientation of flat cells may be aligned hydrodynamically.

Having described preferred embodiments of the invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. A particle analyzer for analyzing particles by passing a sheath liquid around a liquid specimen containing particles to be analyzed, and means for emitting light to the liquid specimen flow, the liquid specimen flow being a flat flow which is thin in thickness and broad in width, a one-dimensional image sensor disposed to extend in a direction vertical to the particle flow direction, and producing a signal at every scanning cycle for the particle, and signal processing means for processing the signal from the one-dimensional image sensor, wherein the signal processing means obtains feature parameters of individual particles on the basis of the signal from said one-dimensional image sensor, by processing the signal from the one dimensional image sensor, thereby analyzing the particles on the basis of the difference of the feature parameters of each particles, said feature parameters containing at least one of particle morphological information and absorption information, said signal processing means comprises:

background correction processing means for obtaining correction data $Sc(i)$, by calculating the difference between background data $Sa$ obtained from the signal from the one-dimensional image sensor in the absence of a particle, and measured data $Sb(i)$ obtained from the signal from the one-dimensional image sensor when a particle is passing through the imaging region, binarizing processing means for obtaining binary signal $Sd(i)$ for detecting the specified portion of the particle by comparing the correction data $Sc(i)$ from the background correction processing means with specified threshold data, binary signal processing means for logical operation for the binary signal from the binarizing processing means, and arithmetic means for calculating said feature parameters by using the binary signal from said binary signal processing means.

2. A particle analyzer of claim 1, further comprising a second light source, and second imaging means for capturing the two-dimensional still image of the particle, wherein a one-dimensional imaging region of the one-dimensional image sensor is formed so as to cross the flow of particle, in a two-dimensional imaging region of the second imaging means in the liquid specimen flow, and the signal processing means detects the arrival of particle on the basis of the imaging signal at least from the one-dimensional image sensor, thereby controlling to illuminate the second light source for capturing two-dimensional still image.

3. A particle analyzer of claim 1, further comprising means for detecting scattered light or fluorescent light emitted from a passing particle, so that the data concerning the scattered light or fluorescent light are ignored when plural particles pass simultaneously and are detected by the one-dimensional image sensor.

4. A particle analyzer of claim 1, wherein the morphological information is at least one selected from cell area, cell circumferential length, cell nucleus area, cell width, cell complicatedness, cell roundness, and nucleus area rate, and wherein the absorption information is at least one selected from absorption quantity and absorptive degree of the particles being analyzed.

5. A particle analyzer of claim 1, further comprising first processing means for obtaining an AND signal $S3(i)$ by a logical AND operation between a binary signal $S2(i)$ of a scan cycle (i) and a binary signal $S2(i-1)$ of one scan cycle before (i-1), and means for obtaining the sum of widths of AND signal pulses corresponding to one particle, means for setting particle moving extent data $L$ in one scanning period, and arithmetic means for multiplying the sum of the widths of the AND signal pulses by particle moving extent data $L$, whereby area data of the particle being analyzed is obtained.

6. A particle analyzer of claim 1, further comprising second processing means for obtaining EXOR signal $S6(i)$ by exclusive-or operation between the binary signal $S2(i)$ of scan cycle i and binary signal $S2(i-1)$ of one scan cycle before i-1, means for obtaining the width of each EXOR signal pulse corresponding to one particle, means for setting the particle moving extent data $L$ in one scanning period, arithmetic means for calculating the square root of the sum of the squared width of each EXOR signal pulse and squared particle moving extent data $L$ in every EXOR signal pulse, and arithmetic means for obtaining the cumulative sum of same particle of the square root data from the arithmetic means, whereby circumferential length data of the particle being analyzed is obtained.

7. A particle analyzer of claim 1, further comprising second processing means for obtaining EXOR signal $S6(i)$ by exclusive-or operation between the binary signal $S2(i)$ of scan cycle i and binary signal $S2(i-1)$ of one scan cycle before i-1, means for obtaining the sum of widths of EXOR signal pulses corresponding to one particle, and arithmetic means for dividing the sum of widths of EXOR signal pulses by 2, whereby the width data of the particle being analyzed in the direction vertical to the moving direction is obtained.

8. A particle analyzer of claim 1, further comprising arithmetic means for obtaining the cumulative sum of the corrected data corresponding to one particle, thereby obtaining absorption quantity data of said corresponding one particle.

9. A particle analyzer of claim 1, further comprising third processing means for obtaining AND signal S3(i) in scan cycle i by logical AND operation between the binary signal S2(i) of scan cycle i and binary signal S2(i−1) of one scan cycle before i−1, and obtaining EXOR signal S7(i) by exclusive-or operation between the AND signal S3(i) of scan cycle i and AND signal S3(i−1) of one scan cycle before i−1, and means for obtaining the width for obtaining the EXOR signal pulse, means for setting the particle moving extent data L in one scanning period, arithmetic means for calculating the square root of the sum of the squared width of each EXOR signal pulse and squared particle moving extent data L in every EXOR signal pulse, and arithmetic means for obtaining cumulative sum for one particle of square root data from the arithmetic means, whereby circumferential length data is obtained.

10. A particle analyzer of claim 1, further comprising third processing means for obtaining AND signal S3(i) in scan cycle i by logical AND operation between the binary signal S2(i) of scan cycle i and binary signal S2(i−1) of one scan cycle before i−1, and obtaining EXOR signal S7(i) by exclusive-or operation between the AND signal S3(i) of scan cycle i and AND signal S3(i−1) of one scan cycle before i−1, means for obtaining the sum of widths of EXOR signal pulses corresponding to one particle, and arithmetic means for dividing the sum of widths of EXOR signal pulses by 2, whereby the width data of the particle being analyzed in the direction vertical to the moving direction is obtained.

11. A particle analyzer of claim 1, further comprising two signal processing means for obtaining binary signals by two different threshold data Th1, Th2, obtaining binary signal S2(i) for the entire particle and the binary signal S4(i) for detecting the nucleus portion of particle, and obtaining AND signals S3(i), S5(i) by logical AND operation between binary signals S2(i), S4(i) of scan cycle i, and binary signals S2(i−1), S4(i−1) of one scan cycle before i−1, corresponding to these two kinds of signals, and means for obtaining the sum of the widths of AND signal pulses corresponding to one particle as the particle area data and nucleus area data, and arithmetic means for dividing the nucleus area data by the particle area data, whereby the nucleus area rate data is obtained.

12. A particle analyzer of claim 1, further comprising arithmetic means for obtaining the cumulative sum of the portion of the nucleus of the individual particles of the correction data, thereby obtaining the absorption quantity data of the nucleus portion.

13. A particle analyzer of claim 5, further comprising differentiating means for obtaining the difference of the adjacent data of each A-D converted data, said A-D converted data is obtained by sampling the corrected data by clocks, and by A-D converting said sampling data, means for obtaining the sum of the differential data of the portion corresponding to one particle, or the sum of the square of the differential data as the complicated quantity data, and arithmetic means for dividing the complicated quantity data by the area data from the arithmetic means for obtaining the area data, thereby obtaining the complicated degree data per unit area.

14. A particle analyzer of claim 6, further comprising arithmetic means for squaring the circumferential length data from the arithmetic means for obtaining the circumferential length and dividing by the area data from the arithmetic means for obtaining the area, thereby obtaining roundness data of the particle being analyzed.

15. A particle analyzer of claim 1, further comprising plural sets of arithmetic means so that feature parameters of particles may be calculated simultaneously if plural particles simultaneously cross the imaging area of the one-dimensional image sensor.

16. A particle analyzer of claim 9, further comprising arithmetic means for squaring the circumferential length data from the arithmetic means for obtaining the circumferential length and dividing by the area data from the arithmetic means for obtaining the area, thereby obtaining roundness data of the particle being analyzed.

17. A particle analyzer of claim 11, further comprising plural sets of arithmetic means so that feature parameters of particles may be calculated simultaneously if plural particles simultaneously cross the imaging area of the one-dimensional image sensor.

* * * * *

UNITED STATES PATENT AND TRADEMARK OFFICE
CERTIFICATE OF CORRECTION

PATENT NO. : 5,548,395
DATED : August 20, 1996
INVENTOR(S) : Tokihiro Kosaka

It is certified that error appears in the above-indentified patent and that said Letters Patent is hereby corrected as shown below:

Column 24,

Claim 17, line 1, "11" should be --8--.

Signed and Sealed this

Seventeenth Day of December, 1996

Attest:

BRUCE LEHMAN

*Attesting Officer*   *Commissioner of Patents and Trademarks*